United States Patent
Chun et al.

(10) Patent No.: US 9,845,492 B2
(45) Date of Patent: *Dec. 19, 2017

(54) TSG PRIMER TARGET DETECTION

(75) Inventors: Jong Yoon Chun, Seoul (KR); In Taek Hwang, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/515,975

(22) PCT Filed: Mar. 26, 2010

(86) PCT No.: PCT/KR2010/001873
§ 371 (c)(1),
(2), (4) Date: Jun. 14, 2012

(87) PCT Pub. No.: WO2011/078441
PCT Pub. Date: Jun. 30, 2011

(65) Prior Publication Data
US 2012/0264643 A1  Oct. 18, 2012

(30) Foreign Application Priority Data

Dec. 21, 2009 (KR) .................. 10-2009-0127880

(51) Int. Cl.
C12Q 1/68 (2006.01)
(52) U.S. Cl.
CPC .................. *C12Q 1/6816* (2013.01)
(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 5,210,015 A | 5/1993 | Gelfand et al. |
| 5,487,972 A | 1/1996 | Gelfand et al. |
| 5,538,848 A | 7/1996 | Livak et al. |
| 5,723,591 A | 3/1998 | Livak et al. |
| 6,117,635 A | 9/2000 | Nazarenko et al. |
| 6,248,526 B1 | 6/2001 | Welmer |
| 6,322,980 B1 | 11/2001 | Singh |
| 6,326,145 B1 | 12/2001 | Whitcombe et al. |
| 6,383,752 B1* | 5/2002 | Agrawal ............ C12Q 1/6816 435/6.1 |
| 7,205,105 B2* | 4/2007 | Afonina ............ C07C 245/08 435/6.1 |
| 7,344,830 B2 | 3/2008 | Philpott et al. |
| 7,537,886 B1 | 5/2009 | Nazarenko et al. |
| 7,759,126 B2* | 7/2010 | Lokhov ............ C07H 21/04 436/94 |
| 2002/0064772 A1 | 5/2002 | Gildea ............ C07K 14/003 435/5 |
| 2003/0162184 A1* | 8/2003 | Chou ............ C12Q 1/686 435/6.12 |
| 2004/0076994 A1 | 4/2004 | Yaku et al. |
| 2005/0272053 A1* | 12/2005 | Mao ............ C12Q 1/6818 435/6.12 |
| 2007/0048758 A1* | 3/2007 | Lokhov et al. ............ 435/6 |
| 2007/0054296 A1 | 3/2007 | Piepenburg et al. |
| 2007/0099211 A1 | 5/2007 | Aivazachvili et al. |
| 2007/0254284 A1* | 11/2007 | Zhao ............ C12Q 1/6818 435/6.11 |
| 2007/0292868 A1* | 12/2007 | Madejon Seiz ...... C12Q 1/6823 435/6.1 |
| 2009/0068643 A1* | 3/2009 | Behlke ............ C12Q 1/6823 435/6.16 |
| 2009/0081676 A1 | 3/2009 | Chou et al. |
| 2012/0219955 A1* | 8/2012 | Chun ............ C12Q 1/6818 435/6.11 |

FOREIGN PATENT DOCUMENTS

| | | |
|---|---|---|
| EP | 1634962 A1 | 3/2006 |
| WO | 1988010315 | 12/1988 |
| WO | 1989006700 | 7/1989 |

(Continued)

OTHER PUBLICATIONS

Zhang et al, Journal of Biochemistry and Molecular Biology, vol. 36, No. 6, Nov. 2003, pp. 525-528.*
Nazarenko et al, Nucleic Acids Research, 1997, vol. 25, No. 12, p. 2516-2521.*
Stratagene PFU Polymerase Manual, 2004.*
Mercier et al, Biophysical Journal, vol. 85, Oct. 2003, p. 2075-2086.*
Marras et al, Genetic Analysis: Biomolecular Engineering (1999), p. 151-156.*
Limones et al. (A novel quantitative real-time PCR test for *Mycobacterium tuberculosis*, Clinical Laboratory Int'l, Oct. 1, 2006).*
Fiandaca et al. (Self-Reporting PNA/DNA Primers for PCR Analysis, Genome Res. Apr. 2001;11(4):609-13).*
Liu et al. (TagMan probe array for quantitative detection of DNA targets, Nucleic Acids Res. 2006; 34(1): e4, Published online Jan. 10, 2006).*
Stratagene (Gene Characterization Kits; 1988).*

(Continued)

*Primary Examiner* — Aaron A Priest
(74) *Attorney, Agent, or Firm* — Gianna Julian-Arnold; Saul Ewing Arnstein & Lehr LLP

(57) ABSTRACT

The present invention relates to the detection of a target nucleic acid sequence in a real-time manner using a target signal generating primer (TSG primer) having dual interactive labels. The present invention allows for both target amplification and signal amplification by introducing dual interactive labels into a primer used in PCR reactions, ensuring real-time target detection by PCR reactions without the use of complicated oligonucleotides. The present invention could be free from the troublesome matters and shortcomings associated with conventional real-time PCR methods. The present invention allows for successful real-time target detection by using only a labeled primer. Also, the present invention can obtain strong signals indicative of the presence of target nucleic acid sequences in both a liquid phase and solid phase.

7 Claims, 21 Drawing Sheets

(56) References Cited

FOREIGN PATENT DOCUMENTS

WO      2006/095981 A1     9/2006

OTHER PUBLICATIONS

Weiner et al. (Kits and their unique role in molecular biology: a brief retrospective, BioTechniques 44:701-704 (25th Anniversary Issue, Apr. 2008)).*

Chun et al. (Dual priming oligonucleotide system for the multiplex detection of respiratory viruses and SNP genotyping of CYP2C19 gene, Nucleic Acids Res. 2007;35(6):e40. Epub Feb. 7, 2007).*

International Search Report, dated Mar. 1, 2011, issued in priority International Application No. PCT/KR2010/001873.

Marras et al., Clinica Chimica Acta., vol. 363, pp. 48-60 (2005).

Whitcombe, David, et al., Detection of PCR products using self-probing amplicons and fluorescence, 1999 Nature America Inc., Nature Biotechnology, Aug. 1999, vol. 17, pp. 804-807.

Parashar, Deepti, D.S., et al., Applications of real-time PCR technology to mycobacterial research, Indian J Med Res 124, Oct. 2006, pp. 385-398.

Tyagi, Sanjay, et al., Molecular Beacons: Probes that Fluoresce upon Hybridization, Nature Biotechnology, Mar. 1996, vol. 14, pp. 303-308.

Bernard, Philip S., et al., Homogeneous Amplification and Variant Detection by Fluorescent Hybridization Probes, Clinical Chemistry 46, No. 2, 2000, pp. 147-148.

Kwoh, D., et al., Transcription-based amplification system and detection of amplified human immunodeficiency virus type 1 with a bead-based sandwich hybridization format, Proc. Natl. Acad. Sci, USA, Feb. 1989, vol. 86, pp. 1173-1177.

Saiki, R., et al., Enzymatic Amplification of $\beta$-Globin Genomic Sequences and Restriction Site Analysis for Diagnosis of Sickle Cell Anemia, Science, Dec. 1985, vol. 230, pp. 1350-1354.

Noonan, K., et al., mRNA phenotyping by enzymatic amplification of randomly primed cDNA, Nucleic Acids Research, 1988, vol. 16, No. 21, p. 10366.

Nazarenko, I., et al., A closed tube format for amplification and detection of DNA based on energy transfer, Nucleic Acids Research, 1997, vol. 25, No. 12, pp. 2516-2521.

\* cited by examiner

Fig. 1A

Real-time signal generation

A-1. Hybridization and signal generation of TSG primer

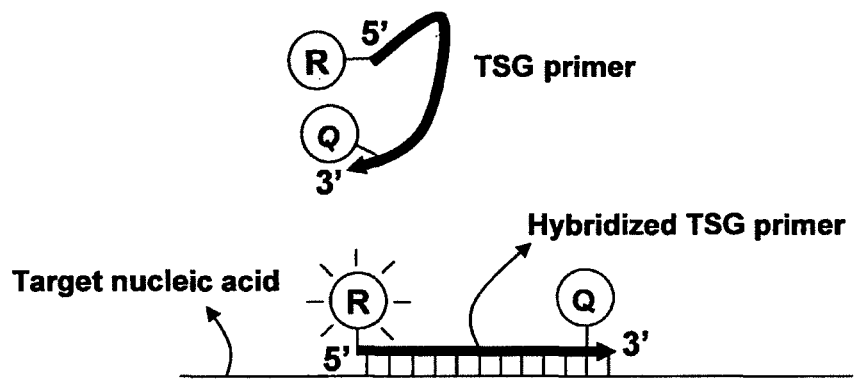

A detectable signal indicative of the presence of a target nucleic acid is obtained by hybridization between a TSG primer and a target nucleic acid.

 Nucleic acid polymerase having no 5' to 3' nuclease activity

A-2. Extension of TSG primer

A TSG primer is incorporated into the extension product and stabilized.

 : Reporter molecule      : Quencher molecule

Fig. 1B

Real-time signal generation

B-1. Hybridization and signal generation of TSG primer

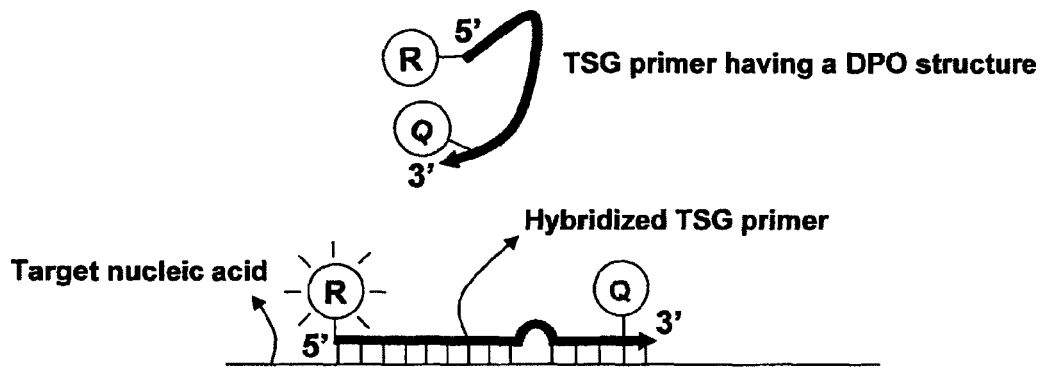

A detectable signal indicative of the presence of a target nucleic acid is obtained by hybridization between a TSG primer and a target nucleic acid.

⇩ Nucleic acid polymerase having no 5' to 3' nuclease activity

B-2. Extension of TSG primer

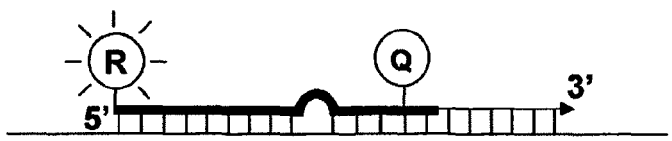

A TSG primer is incorporated into the extension product and stabilized.

 : Reporter molecule       : Quencher molecule

DPO: Dual Priming Oligonucleotide

Fig. 2A

Real-time PCR using TSG primer

A-1. Hybridization and signal generation

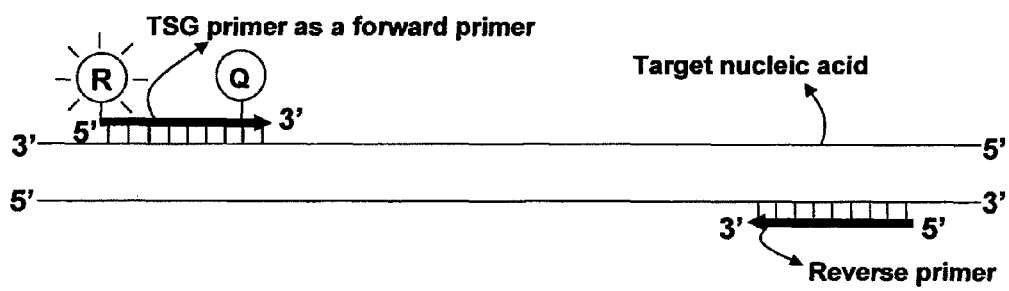

A detectable signal indicative of the presence of a target nucleic acid is obtained by hybridization between a TSG primer and a target nucleic acid.

⇩ Nucleic acid polymerase having no 5' to 3' nuclease activity

A-2. Extension of TSG primer

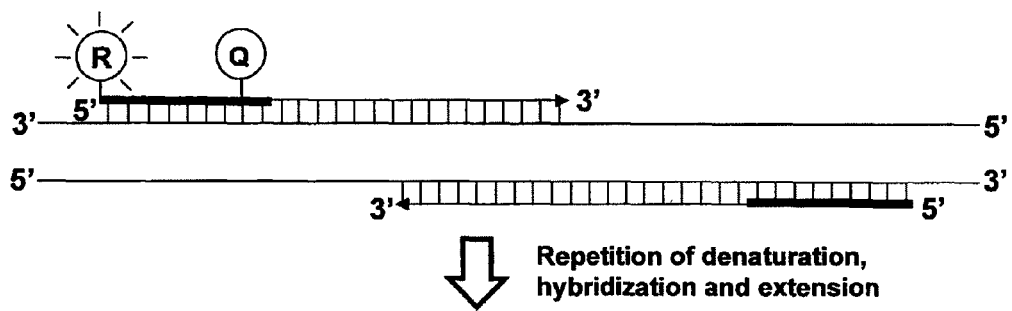

⇩ Repetition of denaturation, hybridization and extension

Real-time amplification and detection of a target nucleic acid (R) : Reporter molecule        (Q) : Quencher molecule

Fig. 2B

Real-time PCR using TSG primer

B-1. Hybridization and signal generation

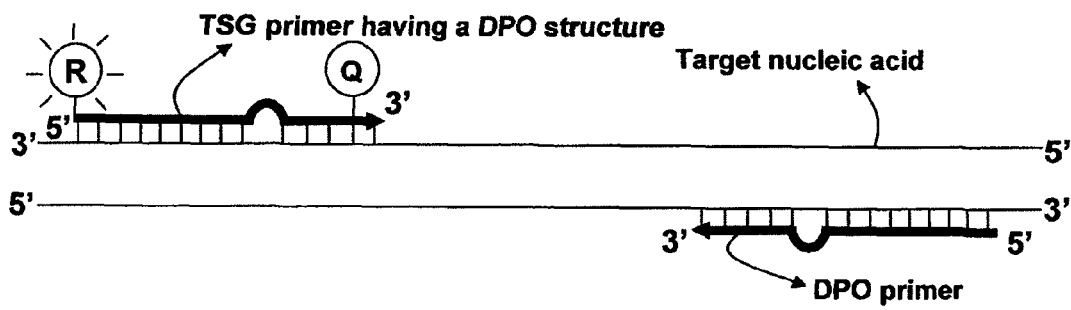

A detectable signal indicative of the presence of a target nucleic acid is obtained by hybridization between a TSG primer and a target nucleic acid.

⇩ Nucleic acid polymerase having no 5' to 3' nuclease activity

B-2. Extension of TSG primer

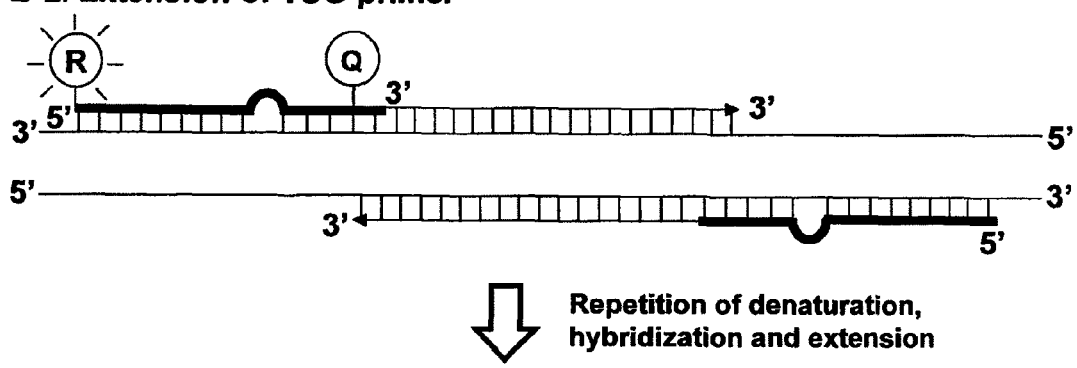

⇩ Repetition of denaturation, hybridization and extension

Real-time amplification and detection of a target nucleic acid (R) : Reporter molecule    (Q) : Quencher molecule DPO: Dual Priming Oligonucleotide

Fig. 3A

Real-time PCR using TSG primer and nucleic acid polymerase having 5' to 3' nuclease activity

A-1. Hybridization and signal generation

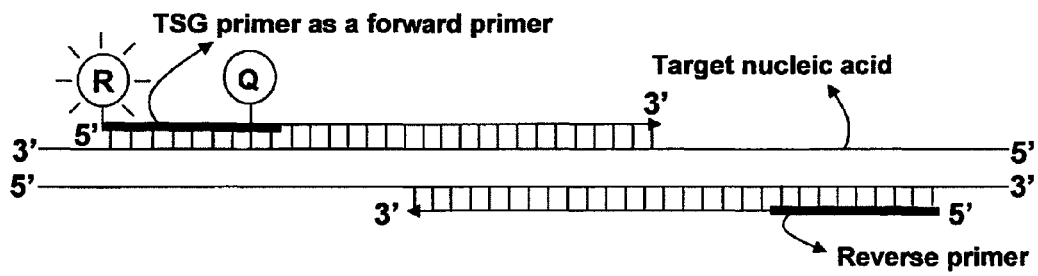

A detectable signal indicative of the presence of the target nucleic acid is obtained by hybridization and extension of a TSG primer.

A-2. 5'-cleavage and 3'-extension of TSG primer

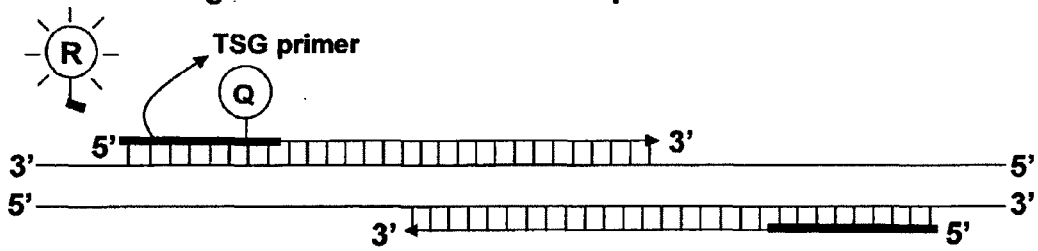

A detectable signal indicative of the presence of the target nucleic acid is obtained by the 5'-cleavage reaction on a TSG primer.

⇩ Repetition of denaturation, hybridization, cleavage and extension

Real-time amplification and detection of a target nucleic acid (R) : Reporter molecule    (Q) : Quencher molecule

Fig. 3B

Real-time PCR using TSG primer and nucleic acid polymerase having 5' to 3' nuclease activity

B-1. Hybridization

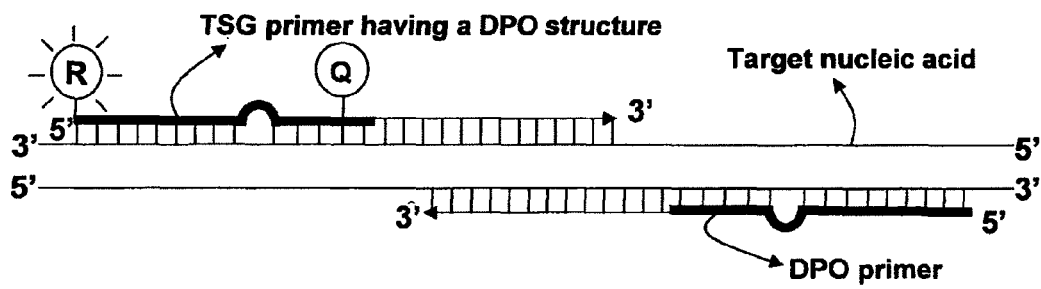

A detectable signal indicative of the presence of the target nucleic acid is obtained by hybridization and extension of a TSG primer.

B-2. 5'-cleavage and 3'-extension of TSG primer

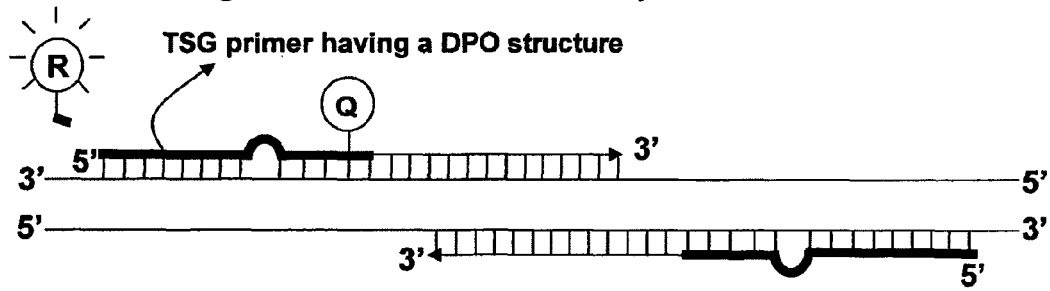

A detectable signal indicative of the presence of the target nucleic acid is obtained by the 5'-cleavage reaction on a TSG primer.

⇩ Repetition of denaturation, hybridization, cleavage and extension

Real-time amplification and detection of a target nucleic acid

 : Reporter molecule    (Q) : Quencher molecule

DPO: Dual Priming Oligonucleotide

Fig. 4A
A-1.
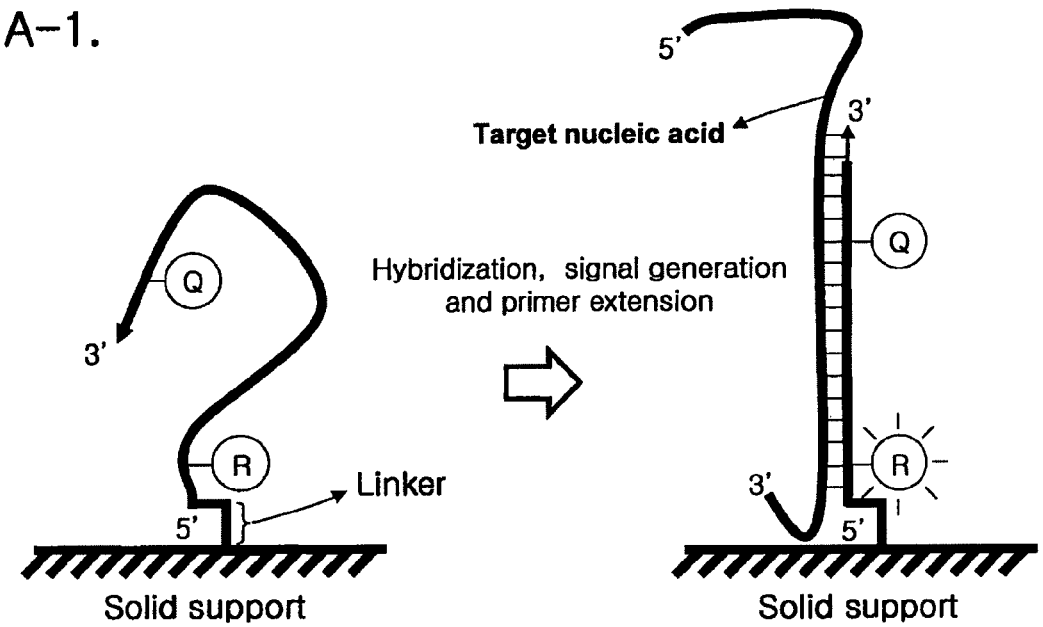
A-2.
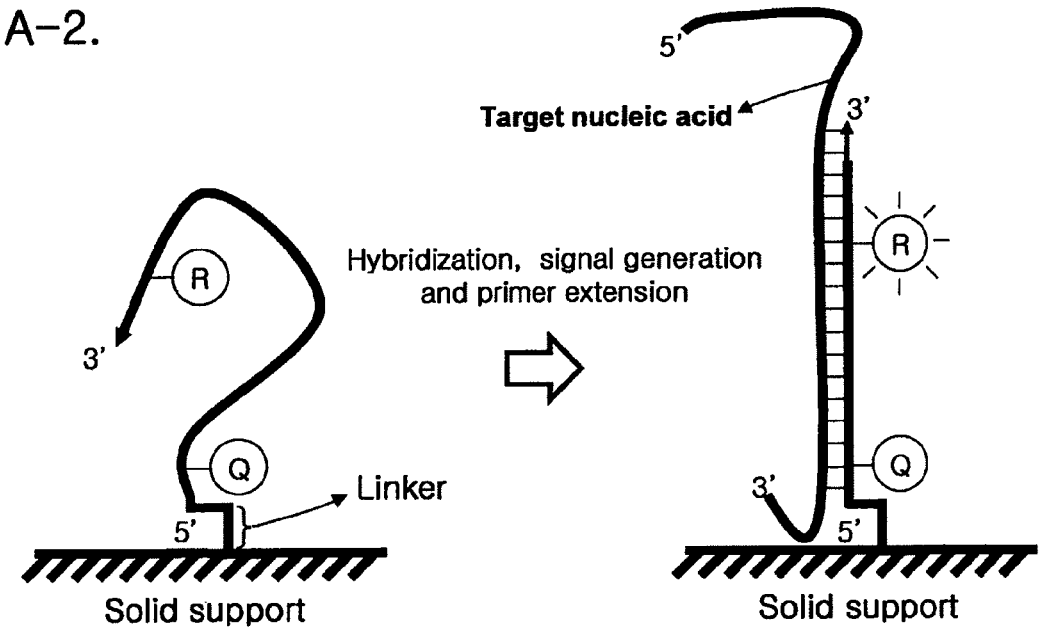
(R) : Reporter molecule    (Q) : Quencher molecule

Fig. 4B
B-1.
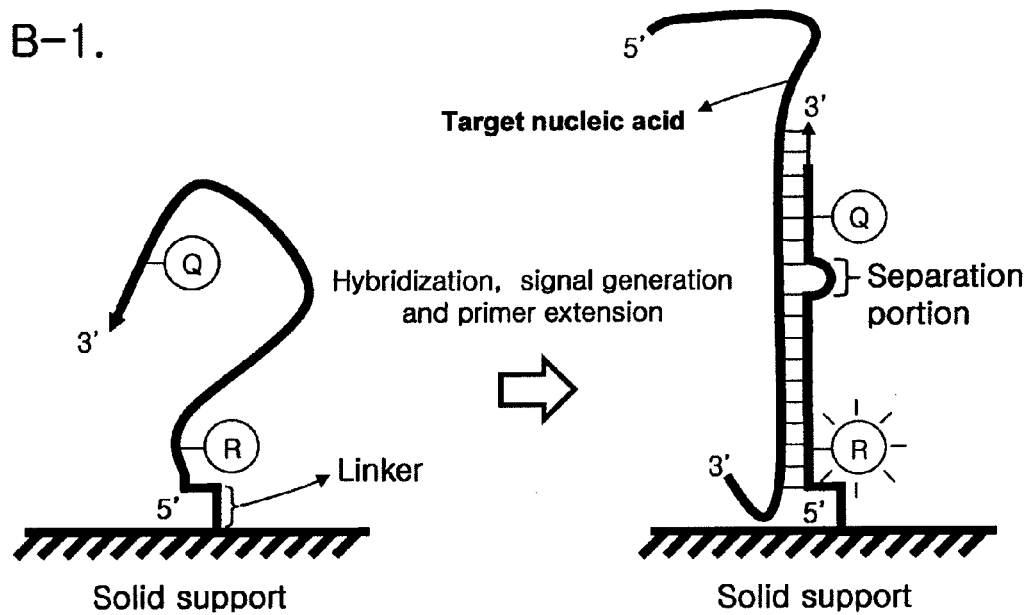
B-2.
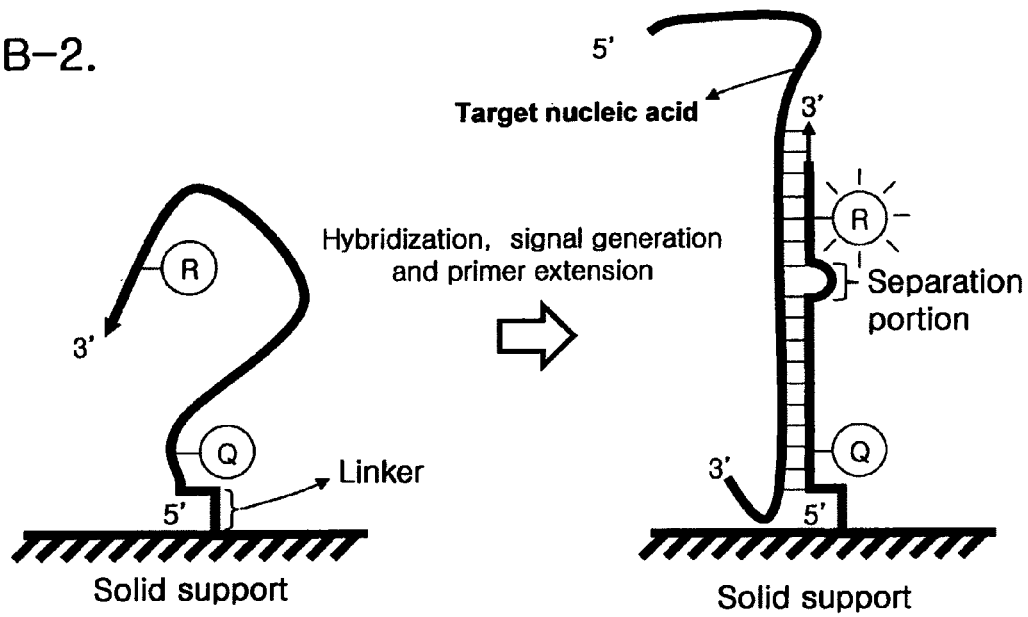

Fig. 5

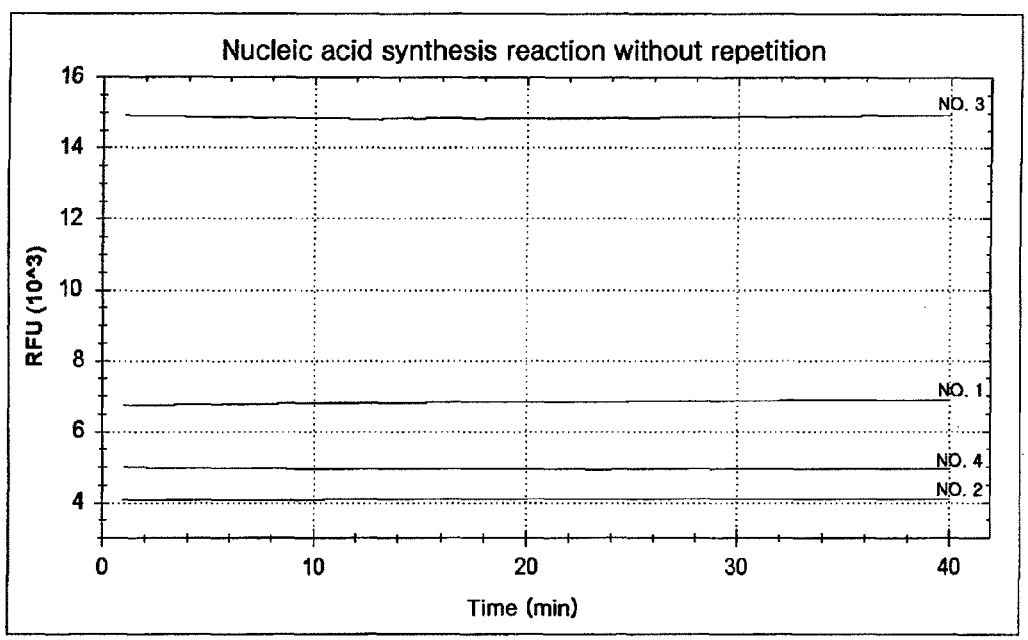

| No. | DNA polymerase [1] | Template [2] | TSG primer [3] | RFU [4] | ΔRFU [5] |
|---|---|---|---|---|---|
| 1 | 5' to 3' Exo⁻ | + | SP_TSG(9) | 6905 | 2794 |
| 2 | 5' to 3' Exo⁻ | − | SP_TSG(9) | 4111 | |
| 3 | 5' to 3' Exo⁻ | + | SP_TSG(21) | 14935 | 9991 |
| 4 | 5' to 3' Exo⁻ | − | SP_TSG(21) | 4944 | |

[1] DNA polymerase is the Stoffel fragment lacking intrinsic 5' to 3' exonuclease activity (5' to 3' Exo⁻).
[2] Template is a synthetic oligonucleotide for *Streptococcus pneumoniae* gene.
[3] TSG primers have the same sequence but a different distance between a reporter molecule and a quencher molecule as indicated in parenthesis.
[4] RFU value is measured at 40 min.
[5] ΔRFU is calculated by subtracting the RFU value with template from the RFU value without template.

Fig. 6

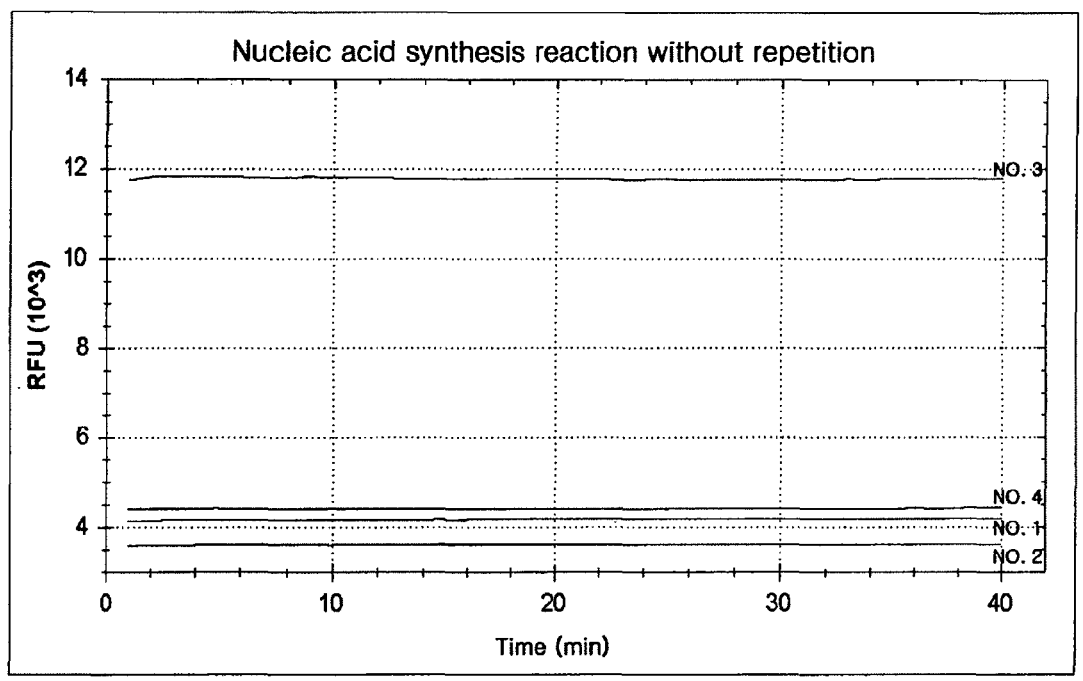

| No. | DNA polymerase [1] | Template [2] | TSG primer [3] | RFU [4] | ΔRFU [5] |
|---|---|---|---|---|---|
| 1 | 5' to 3' Exo⁻ | + | SA_TSG(6) | 4194 | 559 |
| 2 | 5' to 3' Exo⁻ | − | SA_TSG(6) | 3635 | |
| 3 | 5' to 3' Exo⁻ | + | SA_TSG(21) | 11788 | 7365 |
| 4 | 5' to 3' Exo⁻ | − | SA_TSG(21) | 4423 | |

[1] DNA polymerase is the Stoffel fragment lacking intrinsic 5' to 3' exonuclease activity (5' to 3' Exo⁻).
[2] Template is a synthetic oligonucleotide for *Staphylococcus aureus* gene.
[3] TSG primers have the same sequence but a different distance between a reporter molecule and a quencher molecule as indicated in parenthesis.
[4] RFU value is measured at 40 min.
[5] ΔRFU is calculated by subtracting the RFU value with template from the RFU value without template.

Fig. 7

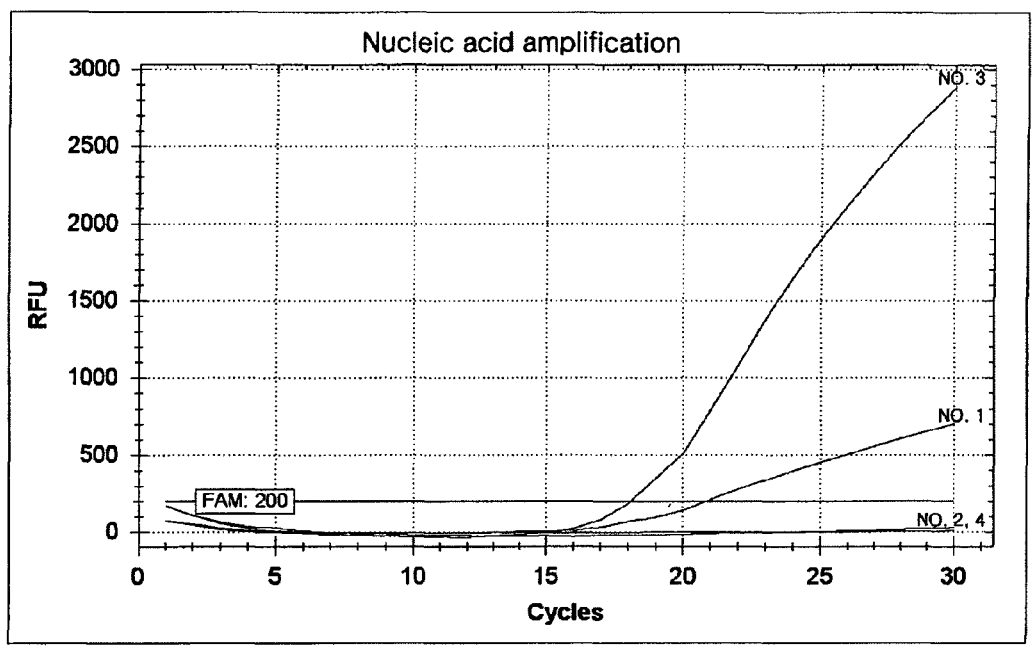

| No. | DNA polymerase [1] | Template [2] | TSG primer [3] | Ct value |
|---|---|---|---|---|
| 1 | 5' to 3' Exo⁻ | + | SP_TSG(9) | 20.83 |
| 2 | 5' to 3' Exo⁻ | − | SP_TSG(9) | − |
| 3 | 5' to 3' Exo⁻ | + | SP_TSG(21) | 18.09 |
| 4 | 5' to 3' Exo⁻ | − | SP_TSG(21) | − |

[1] DNA polymerase is the Stoffel fragment lacking intrinsic 5' to 3' exonuclease activity (5' to 3' Exo−).
[2] Template is a genomic DNA of *Streptococcus pneumoniae*.
[3] TSG primers have the same sequence but a different distance between a reporter molecule and a quencher molecule as indicated in parenthesis.

Fig. 8

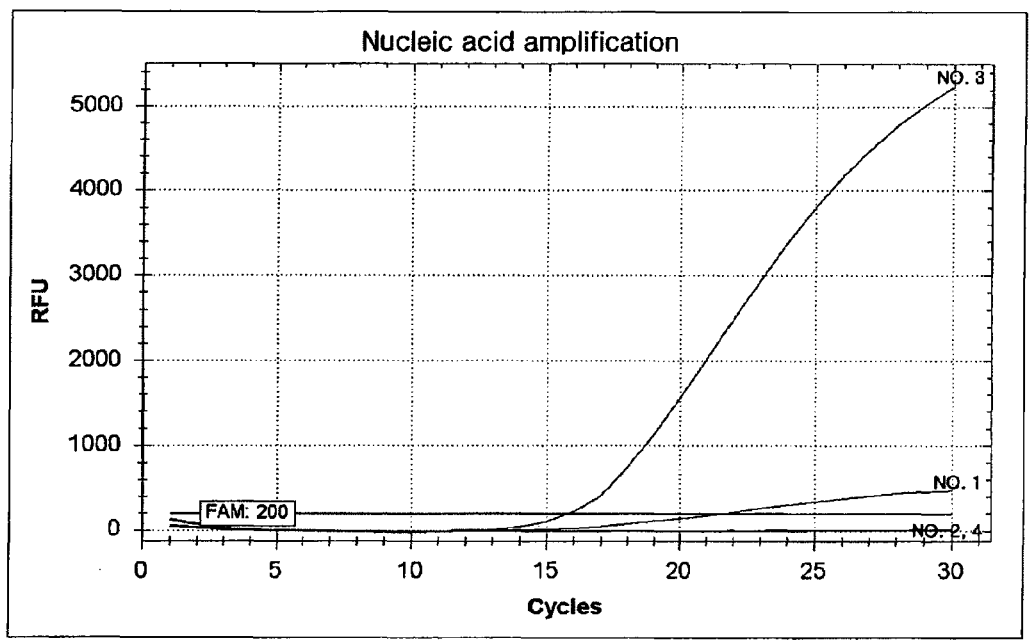

| No. | DNA polymerase [1] | Template [2] | TSG primer [3] | Ct value |
|---|---|---|---|---|
| 1 | 5' to 3' Exo⁻ | + | SA_TSG(6) | 21.63 |
| 2 | 5' to 3' Exo⁻ | − | SA_TSG(6) | − |
| 3 | 5' to 3' Exo⁻ | + | SA_TSG(21) | 15.79 |
| 4 | 5' to 3' Exo⁻ | − | SA_TSG(21) | − |

[1] DNA polymerase is the Stoffel fragment lacking intrinsic 5' to 3' exonuclease activity (5' to 3' Exo−).
[2] Template is a genomic DNA of *Staphylococcus aureus*.
[3] TSG primers have the same sequence but a different distance between a reporter molecule and a quencher molecule as indicated in parenthesis.

Fig. 9

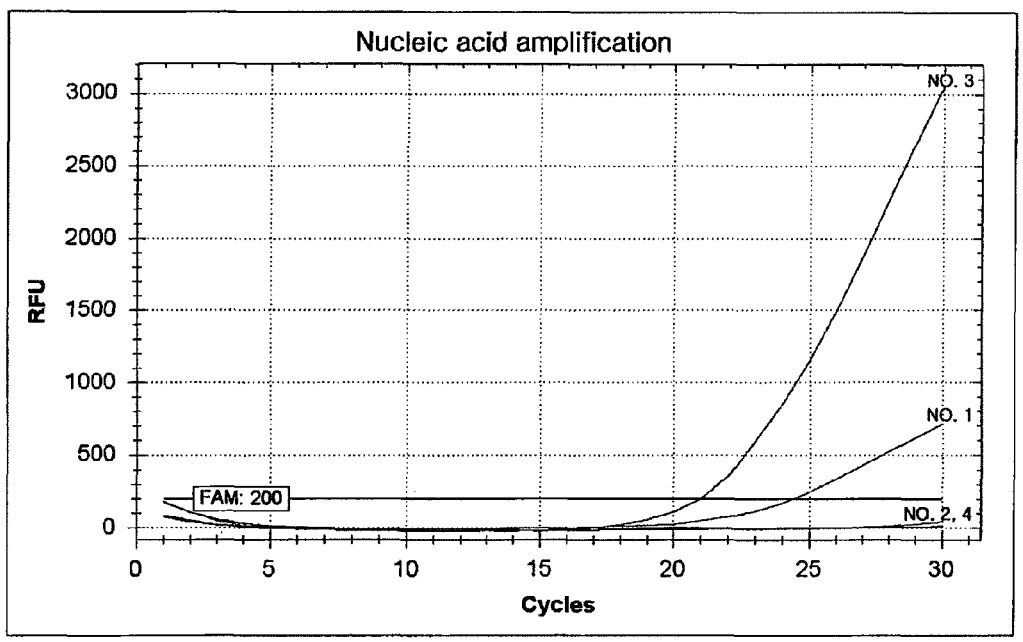

| No. | DNA polymerase [1] | Template [2] | TSG primer [3] | Ct value |
|---|---|---|---|---|
| 1 | 5' to 3' Exo⁻ | + | NG_TSG(4) | 24.37 |
| 2 | 5' to 3' Exo⁻ | − | NG_TSG(4) | − |
| 3 | 5' to 3' Exo⁻ | + | NG_TSG(22) | 20.98 |
| 4 | 5' to 3' Exo⁻ | − | NG_TSG(22) | − |

[1] DNA polymerase is the Stoffel fragment lacking intrinsic 5' to 3' exonuclease activity (5' to 3' Exo−).
[2] Template is a genomic DNA of *Neisseria gonorrhoeae*.
[3] TSG primers have the same sequence but a different distance between a reporter molecule and a quencher molecule as indicated in parenthesis.

Fig. 10

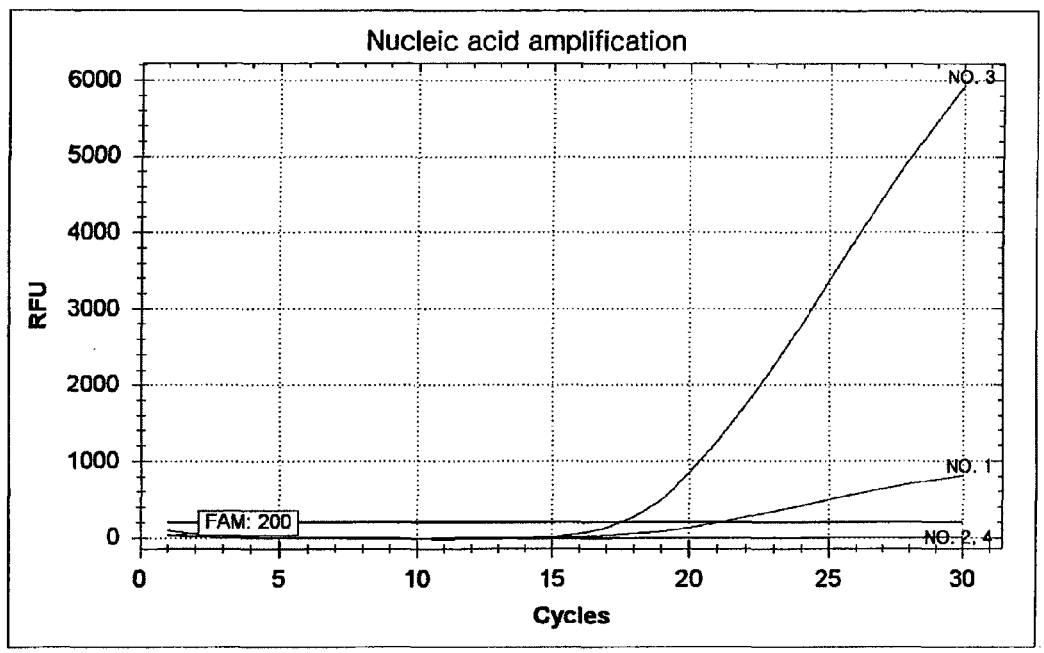

| No. | DNA polymerase [1] | Template [2] | TSG primer [3] | Ct value |
|---|---|---|---|---|
| 1 | 5' to 3' Exo⁻ | + | NM_TSG(7) | 21.05 |
| 2 | 5' to 3' Exo⁻ | − | NM_TSG(7) | − |
| 3 | 5' to 3' Exo⁻ | + | NM_TSG(20) | 17.49 |
| 4 | 5' to 3' Exo⁻ | − | NM_TSG(20) | − |

[1] DNA polymerase is the Stoffel fragment lacking intrinsic 5' to 3' exonuclease activity (5' to 3' Exo−).
[2] Template is a genomic DNA of *Neisseria meningitidis*.
[3] TSG primers have the same sequence but a different distance between a reporter molecule and a quencher molecule as indicated in parenthesis.

Fig. 11

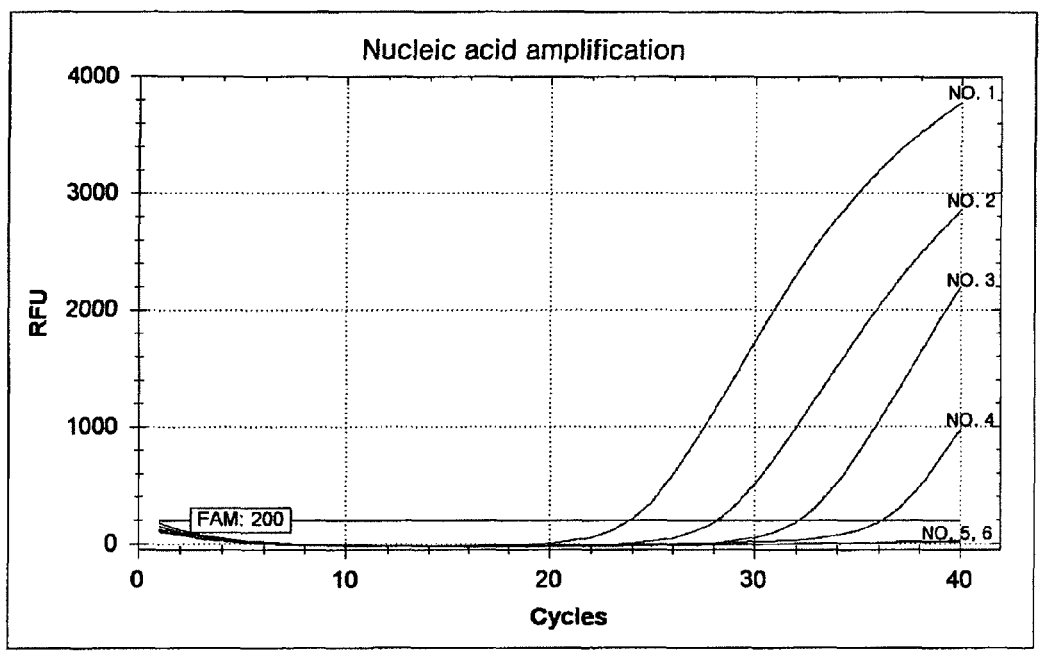

| No. | DNA polymerase [1] | TSG primer [2] | Template [3] | Ct value |
|---|---|---|---|---|
| 1 | 5' to 3' Exo⁻ | SA_TSG(21) | 100 pg | 23.92 |
| 2 | 5' to 3' Exo⁻ | SA_TSG(21) | 10 pg | 28.19 |
| 3 | 5' to 3' Exo⁻ | SA_TSG(21) | 1 pg | 32.16 |
| 4 | 5' to 3' Exo⁻ | SA_TSG(21) | 100 fg | 36.16 |
| 5 | 5' to 3' Exo⁻ | SA_TSG(21) | 10 fg | – |
| 6 | 5' to 3' Exo⁻ | SA_TSG(21) | – | – |

[1] DNA polymerase is the Stoffel fragment lacking intrinsic 5' to 3' exonuclease activity (5' to 3' Exo-).

[2] TSG primer has a distance of 21 nucleotides between a reporter molecule and a quencher molecule as indicated in parenthesis.

[3] Template is a serial diluted genomic DNA of *Staphylococcus aureus* as indicated.

Fig. 12

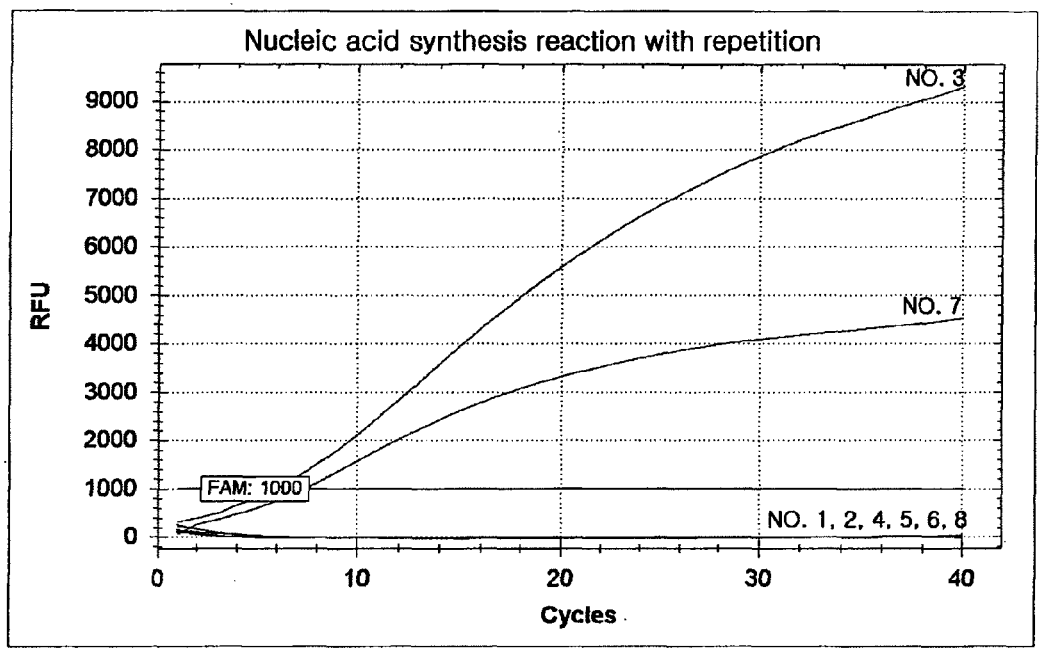

| No. | TSG primer [1] | DNA polymerase | Template [4] | Ct value |
|---|---|---|---|---|
| 1 | SP_TSG(9) | 5' to 3' Exo⁻ [2] | + | – |
| 2 | | | – | – |
| 3 | SP_TSG(9) | 5' to 3' Exo⁺ [3] | + | 5.85 |
| 4 | | | – | – |
| 5 | SP_TSG(21) | 5' to 3' Exo⁻ | + | – |
| 6 | | | – | – |
| 7 | SP_TSG(21) | 5' to 3' Exo⁺ | + | 7.36 |
| 8 | | | – | – |

[1] TSG primers have the same sequence but a different distance between a reporter molecule and a quencher molecule as indicated in parenthesis.
[2] 5' to 3' Exo⁻ is the Stoffel fragment lacking intrinsic 5' to 3' exonuclease activity.
[3] 5' to 3' Exo⁺ is a *Taq* DNA polymerase having 5' to 3' exonuclease activity.
[4] Template is a synthetic oligonucleotide for *Streptococcus pneumoniae* gene.

Fig. 13

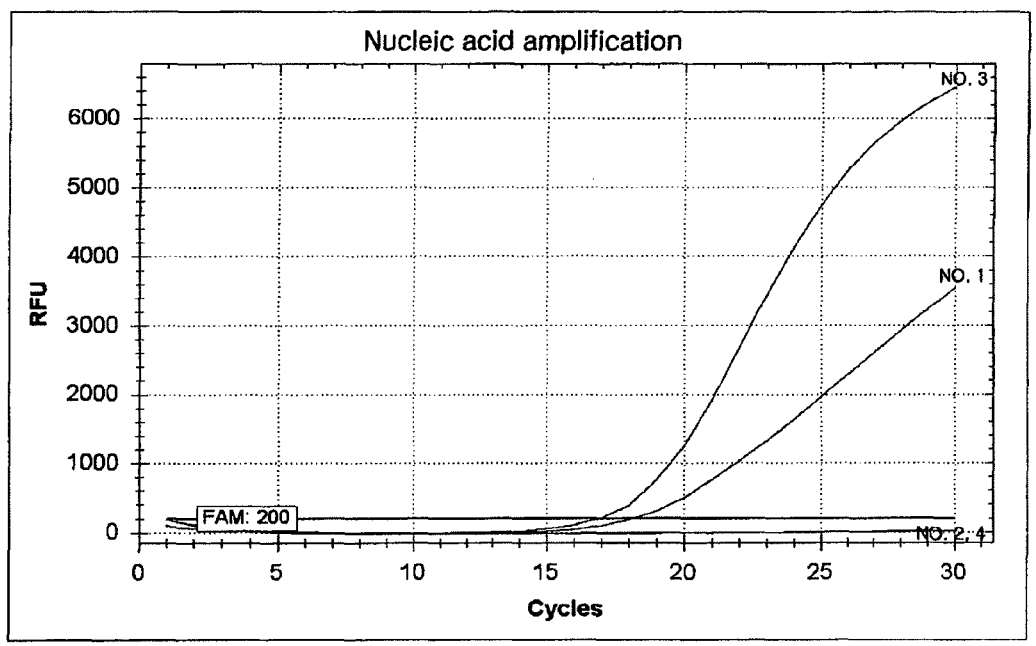

| No. | DNA polymerase [1] | Template [2] | TSG primer [3] | Ct value |
|---|---|---|---|---|
| 1 | 5' to 3' Exo+ | + | SP_TSG(9) | 18.19 |
| 2 | 5' to 3' Exo+ | − | SP_TSG(9) | − |
| 3 | 5' to 3' Exo+ | + | SP_TSG(21) | 16.96 |
| 4 | 5' to 3' Exo+ | − | SP_TSG(21) | − |

[1] DNA polymerase is a *Taq* DNA polymerase having 5' to 3' exonuclease activity (5' to 3' Exo+)
[2] Template is a genomic DNA of *Streptococcus pneumoniae*.
[3] TSG primers have the same sequence but a different distance between a reporter molecule and a quencher molecule as indicated in parenthesis.

Fig. 14

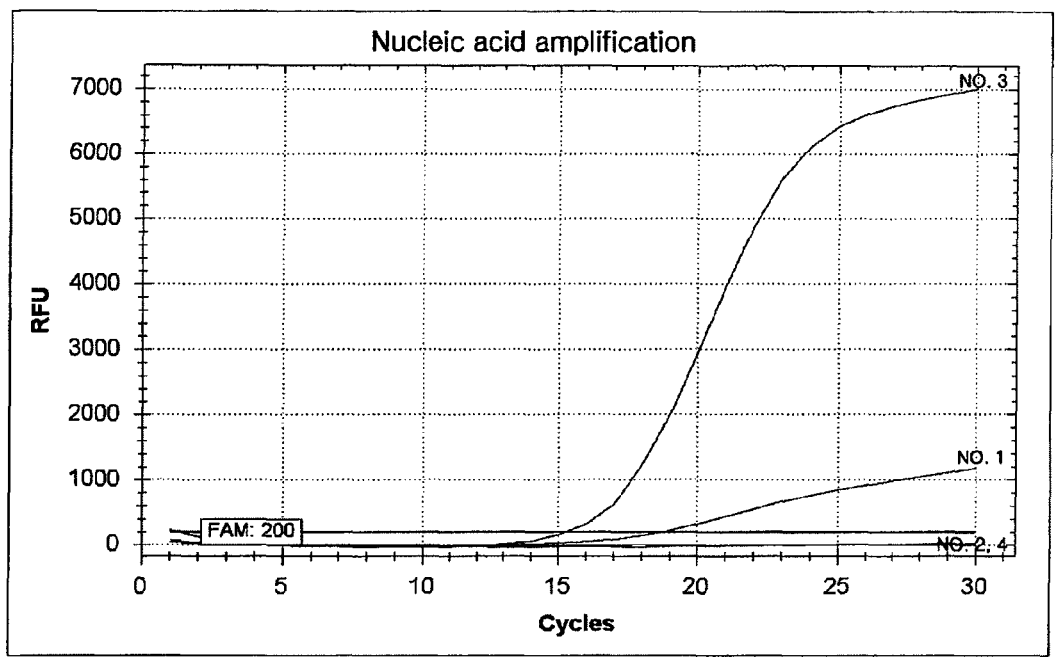

| No. | DNA polymerase [1] | Template [2] | TSG primer [3] | Ct value |
|---|---|---|---|---|
| 1 | 5' to 3' Exo+ | + | SA_TSG(6) | 18.73 |
| 2 | 5' to 3' Exo+ | − | SA_TSG(6) | − |
| 3 | 5' to 3' Exo+ | + | SA_TSG(21) | 15.26 |
| 4 | 5' to 3' Exo+ | − | SA_TSG(21) | − |

[1] DNA polymerase is a *Taq* DNA polymerase having 5' to 3' exonuclease activity (5' to 3' Exo+)
[2] Template is a genomic DNA of *Staphylococcus aureus*.
[3] TSG primers have the same sequence but a different distance between a reporter molecule and a quencher molecule as indicated in parenthesis.

Fig. 15

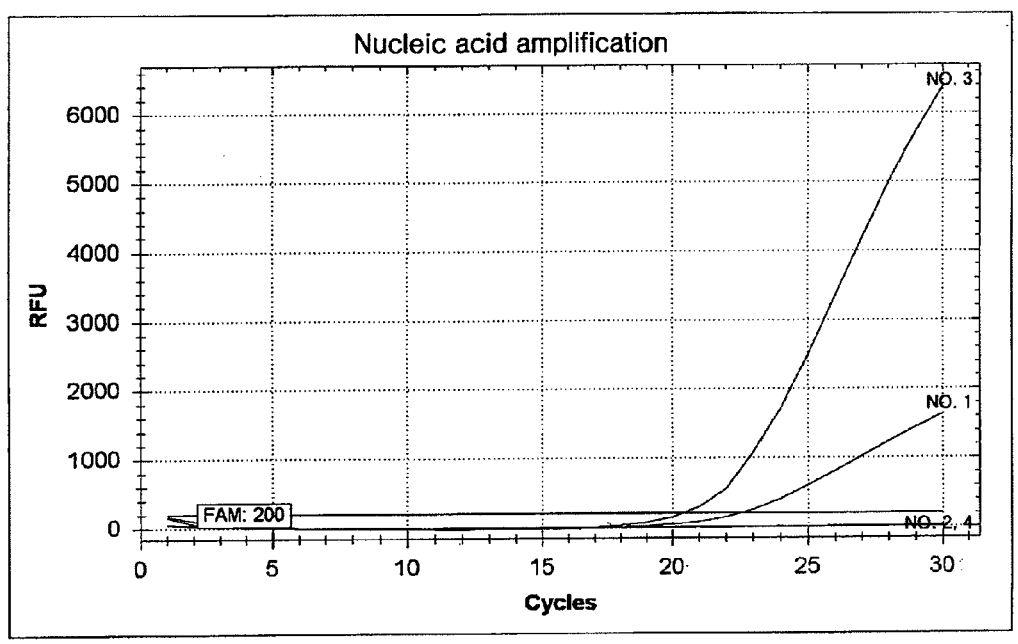

| No. | DNA polymerase [1] | Template [2] | TSG primer [3] | Ct value |
|---|---|---|---|---|
| 1 | 5' to 3' Exo⁺ | + | NG_TSG(4) | 22.59 |
| 2 | 5' to 3' Exo⁺ | – | NG_TSG(4) | – |
| 3 | 5' to 3' Exo⁺ | + | NG_TSG(22) | 20.39 |
| 4 | 5' to 3' Exo⁺ | – | NG_TSG(22) | – |

[1] DNA polymerase is a *Taq* DNA polymerase having 5' to 3' exonuclease activity (5' to 3' Exo⁺)
[2] Template is a genomic DNA of *Neisseria gonorrhoeae*.
[3] TSG primers have the same sequence but a different distance between a reporter molecule and a quencher molecule as indicated in parenthesis.

Fig. 16

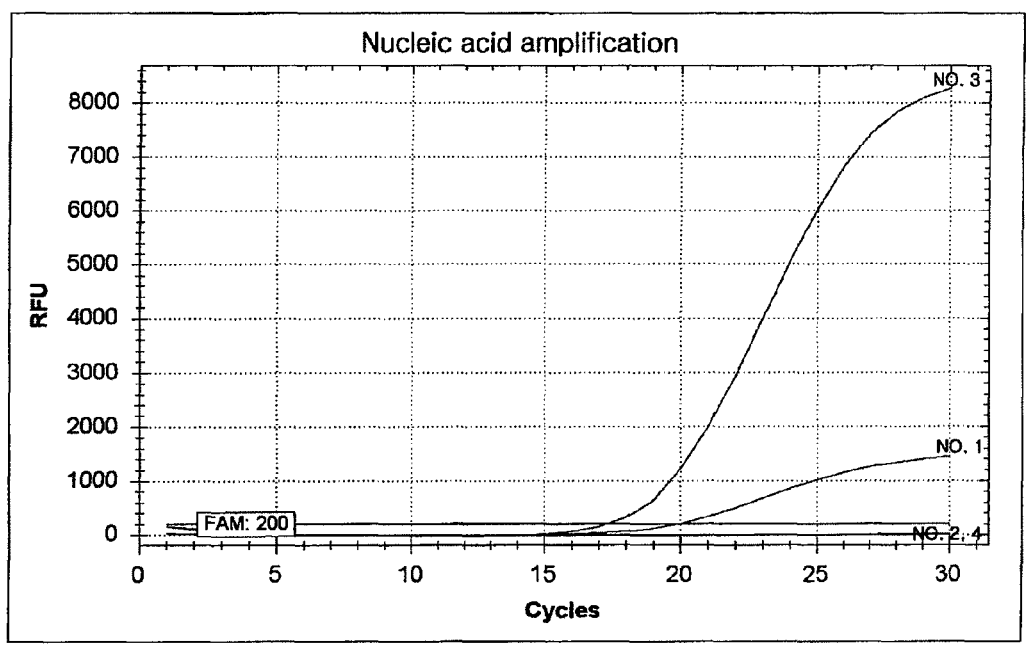

| No. | DNA polymerase [1] | Template [2] | TSG primer [3] | Ct value |
|---|---|---|---|---|
| 1 | 5' to 3' Exo+ | + | NM_TSG(7) | 19.94 |
| 2 | 5' to 3' Exo+ | − | NM_TSG(7) | − |
| 3 | 5' to 3' Exo+ | + | NM_TSG(20) | 17.30 |
| 4 | 5' to 3' Exo+ | − | NM_TSG(20) | − |

[1] DNA polymerase is a *Taq* DNA polymerase having 5' to 3' exonuclease activity (5' to 3' Exo+)
[2] Template is a genomic DNA of *Neisseria meningitidis*.
[3] TSG primers have the same sequence but a different distance between a reporter molecule and a quencher molecule as indicated in parenthesis.

Fig. 17

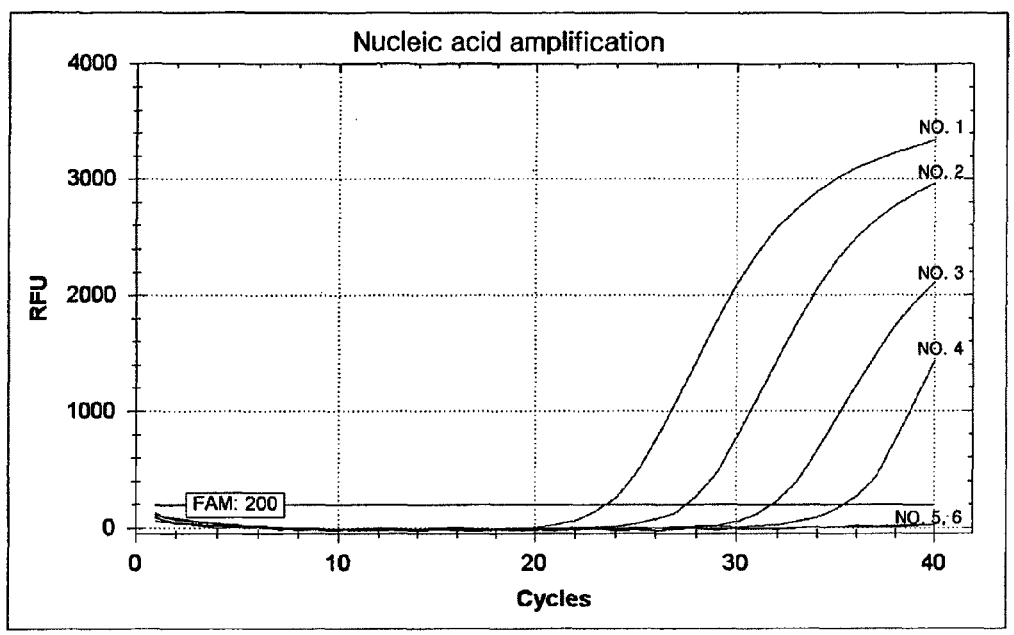

| No. | DNA polymerase [1] | TSG primer [2] | Template [3] | Ct value |
|---|---|---|---|---|
| 1 | 5' to 3' Exo+ | SA_TSG(21) | 100 pg | 23.55 |
| 2 | 5' to 3' Exo+ | SA_TSG(21) | 10 pg | 27.50 |
| 3 | 5' to 3' Exo+ | SA_TSG(21) | 1 pg | 31.74 |
| 4 | 5' to 3' Exo+ | SA_TSG(21) | 100 fg | 35.34 |
| 5 | 5' to 3' Exo+ | SA_TSG(21) | 10 fg | – |
| 6 | 5' to 3' Exo+ | SA_TSG(21) | – | – |

[1] DNA polymerase is a *Taq* DNA polymerase having 5' to 3' exonuclease activity (5' to 3' Exo+)
[2] TSG primer has a distance of 21 nucleotides between a reporter molecule and a quencher molecule as indicated in parenthesis.
[3] Template is a serial diluted genomic DNA of *Staphylococcus aureus* as indicated.

```
                        SEQUENCE LISTING

<160> NUMBER OF SEQ ID NOS: 15

<210> SEQ ID NO 1
<211> LENGTH: 105
<212> TYPE: DNA
<213> ORGANISM: Artificial Sequence
<220> FEATURE:
<223> OTHER INFORMATION: Synthetic Construct; SP_T105 template

<400> SEQUENCE: 1
ttactgaaag acaatgaaga caacctaaca ggggaagatg ttcgcgaagg cttaactgca      60
gttatctcag ttaaacaccc aaatccacag tttgaaggac aaacc                    105

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct; SP_TSG(9) primer

<400> SEQUENCE: 2
tccttcaaac tgtggatttg ggtgt                                           25

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct; SP_TSG(21) primer

<400> SEQUENCE: 3
tccttcaaac tgtggatttg ggtgt                                           25

<210> SEQ ID NO 4
<211> LENGTH: 200
<212> TYPE: DNA
<213> ORGANISM: Artificial Sequence
<220> FEATURE:
<223> OTHER INFORMATION: Synthetic Construct; SA_T200 template

<400> SEQUENCE: 4
gccaataaaa ctaggaggaa atttaaatgt tagaatttga acaaggattt aatcatttag      60
cgactttaaa ggtcattggt gtaggtggtg gcggtaacaa cgccgtaaac cgaatgattg     120
accacggaat gaataatgtt gaattatcg ctatcaacac agacggtcaa gctttaaact     180
tatctaaagc tgaatctaaa                                                200
```

```
<210> SEQ ID NO 5
<211> LENGTH: 24
<212> TYPE: DNA
<213> ORGANISM: Artificial Sequence
<220> FEATURE:
<223> OTHER INFORMATION: Synthetic Construct; SA_TSG(6) primer

<400> SEQUENCE: 5
cattccgtgg tcaatcattc ggtt                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct; SA_TSG(21) primer

<400> SEQUENCE: 6
cattccgtgg tcaatcattc ggtt                                              24

<210> SEQ ID NO 7
<211> LENGTH: 34
<212> TYPE: DNA
<213> ORGANISM: Artificial Sequence
<220> FEATURE:
<223> OTHER INFORMATION: Synthetic Construct; SP_F1 primer
<220> FEATURE:
<221> NAME/KEY: misc_feature
<222> LOCATION: (20)..(24)
<223> OTHER INFORMATION: n denotes deoxyinosine

<400> SEQUENCE: 7
ggtttccgta cagccttgan nnnngttatc aatg                                   34

<210> SEQ ID NO 8
<211> LENGTH: 40
<212> TYPE: DNA
<213> ORGANISM: Artificial Sequence
<220> FEATURE:
<223> OTHER INFORMATION: Synthetic Construct; SA_F1 primer
<220> FEATURE:
<221> NAME/KEY: misc_feature
<222> LOCATION: (26)..(30)
<223> OTHER INFORMATION: n denotes deoxyinosine

<400> SEQUENCE: 8
tgttagaatt tgaacaagga tttaannnnn tagcgacttt                              40

<210> SEQ ID NO 9
<211> LENGTH: 36
<212> TYPE: DNA
<213> ORGANISM: Artificial Sequence
<220> FEATURE:
<223> OTHER INFORMATION: Synthetic Construct; NG_F1 primer
<220> FEATURE:
<221> NAME/KEY: misc_feature
<222> LOCATION: (22)..(26)
<223> OTHER INFORMATION: n denotes deoxyinosine

<400> SEQUENCE: 9
tacgcctgct actttcacgc tnnnnngtaa tcagat                                 36

<210> SEQ ID NO 10
<211> LENGTH: 27
<212> TYPE: DNA
<213> ORGANISM: Artificial Sequence
<220> FEATURE:
```

```
<223> OTHER INFORMATION: NG_TSG(4) primer

<400> SEQUENCE: 10
ctcattggcg tgtttcgcat atttaag                                       27

<210> SEQ ID NO 11
<211> LENGTH: 27
<212> TYPE: DNA
<213> ORGANISM: Artificial Sequence
<220> FEATURE:
<223> OTHER INFORMATION: Synthetic Construct; NG_TSG(22) primer

<400> SEQUENCE: 11
ctcattggcg tgtttcgcat atttaag                                       27

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct; NM_R1 primer
<220> FEATURE:
<221> NAME/KEY: misc_feature
<222> LOCATION: (21)..(25)
<223> OTHER INFORMATION: n denotes deoxyinosine

<400> SEQUENCE: 12
ccataacctt gagcaatcca nnnnncctga cgttc                              35

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct; NM_TSG(7) primer

<400> SEQUENCE: 13
cttatcgctt tctgaagcca ttg                                           23

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct; NM_TSG(20) primer

<400> SEQUENCE: 14
cttatcgctt tctgaagcca ttg                                           23

<210> SEQ ID NO 15
<211> LENGTH: 30
<212> TYPE: DNA
<213> ORGANISM: Artificial Sequence
<220> FEATURE:
<223> OTHER INFORMATION: Synthetic Construct; SP_TSG(21)_S primer

<400> SEQUENCE: 15 tttttttcctt caaactgtgg atttgggtgt                                   30
```

TSG PRIMER TARGET DETECTION

CROSS REFERENCE TO RELATED APPLICATIONS

This application claims the priority of PCT/KR2010/001873, filed on Mar. 26, 2010, which claims the benefit of priority to Korean Application No. 10-2009-0127880, filed on Dec. 21, 2009, the entire contents of each of which are hereby incorporated in total by reference.

SEQUENCE LISTING

This application incorporates by reference the Sequence Listing contained in an ASCII text file named "361406-00012 ST25.txt" submitted via EFS-Web. The text file was created on Jun. 14, 2012, and is 3.94 kb in size.

BACKGROUND OF THE INVENTION

Field of the Invention

The present invention relates to the detection of a target nucleic acid sequence using a target signal generating primer (TSG primer).

Description of the Related Art

A target nucleic acid amplification process is prevalently involved in most of technologies for detecting target nucleic acid sequences. Nucleic acid amplification is a pivotal process for a wide variety of methods in molecular biology, such that various amplification methods have been proposed. For example, Miller, H. I. et al. (WO 89/06700) amplified a nucleic acid sequence based on the hybridization of a promoter/primer sequence to a target single-stranded DNA ("ssDNA") followed by transcription of many RNA copies of the sequence. Other known nucleic acid amplification procedures include transcription-based amplification systems (Kwoh, D. et al., *Proc. Natl. Acad. Sci. U.S.A.*, 86:1173 (1989); and Gingeras T. R. et al., WO 88/10315).

The most predominant process for nucleic acid amplification known as polymerase chain reaction (hereinafter referred to as "PCR") is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) *Science* 230, 1350-1354).

PCR-based techniques have been widely used not only for amplification of a target DNA sequence, but also for scientific applications or methods in the fields of biological and medical research, such as reverse transcriptase PCR (RT-PCR), differential display PCR (DD-PCR), cloning of known or unknown genes by PCR, rapid amplification of cDNA ends (RACE), arbitrary priming PCR (AP-PCR), multiplex PCR, SNP genome typing, and PCR-based genomic analysis (McPherson and Moller, (2000) PCR. BIOS Scientific Publishers, Springer-Verlag New York Berlin Heidelberg, NY).

In the meantime, methods for detecting target nucleic acids based on nucleic acid amplification proposed up to now are summarized as follows:

1. Post-PCR Detection Method

The post-PCR method which is typically heterogeneous involves nucleic acid amplification and thereafter detection of amplified products for analyzing target nucleic acid sequence. The conventional post-PCR detection method requires the amplified products to be separated either on the basis of a size differential, which is commonly achieved through the use of gel electrophoresis, or by the immobilization of the product. However, the separation process causes serious problems such as carry over contamination and low-throughput.

2. Real-Time Detection Methods

To overcome problems of the post-PCR method, a real-time PCR method was suggested to detect amplified products in real-time manner and be free from contaminants, making it possible to quantitatively analyze target nucleic acid sequences.

2.1 Labeled Primer-Based Methods 2.1.1 Sunrise Primer Method

This method uses sunrise primers which form hairpin loops at their 5' ends to bring a fluorophore and quencher pair together, thus ensuring low fluorescence. When these primers have been incorporated into a PCR product, the tails become double stranded and the hairpin is unraveled causing the fluorescence to increase (Nazarenko et al, 2516-2521 Nucleic Acids Research, 1997, v. 25 no. 12, and U.S. Pat. No. 6,117,635). However, the sunrise primer method is very inconvenient in that primers are intricately designed to contain a complementary sequence to target nucleic acid sequences and a sequence capable of forming hairpin loops at their 5'-ends. Furthermore, the existence of the hairpin loops in primers deteriorates their hybridization efficiency to target sequences.

2.1.2 Scorpion Primer Method

This method uses scorpion primers containing an integrated signaling system. The primer has a template binding region and the tail comprising a linker and a target binding region. The target binding region is hybridized with a complementary sequence in an extension product of the primer. Afterwards, this target specific hybridization event is coupled to a signaling system wherein hybridization leads to a detectable change. The linker in the tailed primer prevents polymerase mediated chain copying of the tail region of the primer template (Whitcombe et al, 804-807, Nature Biotechnology v. 17 August 1999 and U.S. Pat. No. 6,326,145). Like the sunrise primer method, this tailed primer also has a difficulty in designing and synthesizing primers due to incorporation of a linker to generate amplicon-dependent signals and a target binding region hybridizable with a primer extension product into a primer. Moreover, the existence of hairpin loops in primers decreases their hybridization efficiency to target sequences.

2.1.3 Single-Labeled Primer Method (Lux Method)

The single-labeled primer method uses primers with a single fluorescence label to detect target sequences by observing changes in the fluorescence characteristics on primers upon hybridizing with target sequences (U.S. Pat. No. 7,537,886). This method also recommends the primers to have a hairpin-loop structure for the efficient signal generation. Moreover, the fluorescence characteristics on primers may be altered by various factors such as types of labels, primer sequences around the fluorescence label, position of the fluorescence label on primers and surrounding other components, making it very difficult to optimize primer design.

2.1.4. Lion Method (Using 3' to 5' Nuclease Activity)

This method uses a labeled primer deliberately mismatched in at least one nucleotide at the 3' end of the primer. The labeled primer is incubated with a sample under conditions sufficient to allow hybridization and the sample is subsequently exposed to nucleic acid polymerase having a 3' to 5' proofreading activity, thereby releasing the label or part of the label system (U.S. Pat. No. 6,248,526).

However, the mismatch primer should be intricately designed to contain a mismatch nucleotide at its 3'-end. To make matters worse, the mismatch primer is likely to generate false positive signals by the 3' to 5' proofreading activity even when the 3'-end is mismatched to non-target sequences.

2.2 Labeled Probe-Based Methods 2.2.1 Molecular Beacon Method

Molecular beacons contain fluorescent and quenching dyes, but FRET (fluorescence resonance energy transfer) only occurs when the quenching dye is directly adjacent to the fluorescent dye. Molecular beacons are designed to adopt a hairpin structure while free in solution, bringing the both dyes in close proximity. When a molecular beacon hybridizes to a target, fluorescent and quencher dyes are separated. FRET does not occur and fluorescent dye emits light upon irradiation (Indian J Med Res 124: 385-398 (2006) and Tyagi et al, Nature Biotechnology v. 14 March 1996).

However, there are some drawbacks in the molecular beacon method.

Firstly, the two inverted repeats of the hairpin structure must have complementary counterparts in the target nucleic acid, which in turn requires the presence of inverted repeats in the target as well, a condition that is not generally met. Secondly, the $T_m$ of the loop portion of the hairpin structure with a complementary nucleic acid sequence and the Tm of the stem portion need to be carefully balanced with respect to the temperature of the assay to allow the specific unfolding of the hairpin probe in the presence of the target without unspecific unfolding. Lastly, this method demands additional primers for amplifying target nucleic acid sequences.

2.2.2 Hybridization Probe Methods

This method uses four oligonucleotides: two primers and two probes. Hybridization probes have a single label, one with a donor fluorophore and one with an acceptor fluorophore. The sequence of the two probes are selected so that they can hybridize to the target sequences in a head to tail arrangement, bringing the tow dyes very close to each other, allowing fluorescence resonance energy transfer (FRET). The acceptor dye in one of the probes transfers energy, allowing the other one to dissipate fluorescence at a different wavelength. The amount of fluorescence is directly proportional to the amount of target DNA generated during the PCR process (385-398, Indian 3 Med Res 124, review article October 2006 and 303-308, and Bernad et al, 147-148 Clin Chem 2000; 46).

However, this method is not adoptable to multiplex detection and requires additional primers for amplifying target nucleic acid sequences.

2.2.3 TaqMan Probe Method (Using 5' to 3' Nuclease Activity)

TaqMan probes are designed to hybridize to an internal region of a PCR product. During PCR when the polymerase replicates a template on which a TaqMan probe is bound, the 5' exonuclease activity of the polymerase cleaves the probe. This separates the fluorescent and quenching dyes and FRET no longer occurs (385-398, Indian 3 Med Res 124, review article October 2006 and 303-308, U.S. Pat. No. 5,210,015).

However, this method is limited in the sense that it employs three oligonucleotides (a dual label probe and two primers). This seriously complicates probe design and synthesis, and reaction condition optimization.

2.2.4. Self-Quenching Probe Method (Using 5' to 3' Nuclease Activity)

The self-quenching probe method uses dual-labeled probes having a sequence hybridizable with an internal region of a PCR product (U.S. Pat. No. 5,723,591).

Likely to the TaqMan method, the self-quenching probe method has to use three oligonucleotides (a dual-labeled probe and two primers) for homogeneous assay, which makes it seriously complicate to optimize probe design and reaction conditions.

As described above, most of conventional target detection methods developed hitherto have intrinsic shortcomings which are considered difficult to overcome.

Accordingly, there is a long-felt need for novel approach to detect target nucleic acid sequences in more technical-, time- and cost-effective manner.

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to overcome shortcomings associated with conventional technologies for real-time detection of target nucleic acid sequences. The present inventors have devised novel TSG (target signal generating) primers capable of generating signals depending on hybridization and extension with target nucleic acid sequences, and have in turn constructed various protocols using the primers for detection of target nucleic acid sequences. As results, we have verified that the new protocols or processes exhibit a plausible performance in detection of target nucleic acid sequences, inter alia, real-time detection, and produce signals indicative of the presence of target nucleic acid sequences in both a liquid phase and a solid phase in much stronger and faster manner.

Accordingly, it is an object of this invention to provide a method for detecting a target nucleic acid sequence from a DNA or a mixture of nucleic acids using a target signal generating primer (TSG primer).

It is another object of this invention to provide a method for detecting a target nucleic acid sequence from a DNA or a mixture of nucleic acids using a target signal generating primer (TSG primer) in an amplification reaction.

It is further object of this invention to provide a kit for detecting a target nucleic acid sequence from a DNA or a mixture of nucleic acids using a target signal generating primer (TSG primer).

Other objects and advantages of the present invention will become apparent from the detailed description to follow taken in conjugation with the appended claims and drawings.

BRIEF DESCRIPTION OF THE DRAWINGS

The basic principles of the present invention are outlined in FIGS. 1-4.

FIG. 1 shows the schematic steps involved in an assay for detecting a target nucleic acid sequence using a TSG primer. FIG. 1A shows the use of a TSG primer having a conventional structure for the detection of a target nucleic acid sequence. FIG. 1B shows the use of a TSG primer having a dual priming oligonucleotide (DPO) structure for the primer annealing specificity in the detection of a target nucleic acid sequence.

FIG. 2 shows a schematic representation of a real-time PCR amplification for the detection of a target nucleic acid in a real-time manner using a TSG primer of this invention and a template-dependent nucleic acid polymerase having no 5' to 3' nuclease activity. FIG. 2A shows the use of a TSG primer having a conventional structure for a real-time PCR amplification. FIG. 2B shows the use of a TSG primer having a dual priming oligonucleotide (DPO) structure for the primer annealing specificity in a real-time PCR amplification.

FIG. 3 shows a schematic representation of a real-time PCR amplification for the detection of a target nucleic acid in a real-time manner using a TSG primer of this invention and a template-dependent nucleic acid polymerase having a 5' to 3' nuclease activity. FIG. 3A shows the use of a TSG primer having a conventional structure for a real-time PCR amplification. FIG. 3B shows the use of a TSG primer having a dual priming oligonucleotide (DPO) structure for the primer annealing specificity in a real-time PCR amplification.

FIG. 4 shows the schematic steps involved in an assay for detecting a target nucleic acid sequence using a TSG primer immobilized on solid substrate. FIG. 4A shows the use of a TSG primer having a conventional structure for the detection of a target nucleic acid sequence. FIG. 4B shows the use of a TSG primer having a dual priming oligonucleotide (DPO) structure for the primer annealing specificity in the detection of a target nucleic acid sequence.

FIG. 5 shows the results of S. pneumoniae detection only by hybridization and extension of TSG primers during nucleic acid synthesis reaction using a template-dependent DNA polymerase having no 5' to 3' exonuclease activity without the repetition of denaturation, hybridization, and primer extension.

FIG. 6 shows the results of S. aureus detection only by hybridization and extension of TSG primers during nucleic acid synthesis reaction using a template-dependent DNA polymerase having no 5' to 3' exonuclease activity without the repetition of denaturation, hybridization, and primer extension.

FIG. 7 shows the results of the real-time PCR amplification for the detection of S. pneumoniae using TSG primers and a template-dependent DNA polymerase having no 5' to 3' exonuclease activity.

FIG. 8 shows the results of the real-time PCR amplification for the detection of S. aureus using TSG primers and a template-dependent DNA polymerase having no 5' to 3' exonuclease activity.

FIG. 9 shows the results of the real-time PCR amplification for the detection of N. gonorrhoeae using TSG primers and a template-dependent DNA polymerase having no 5' to 3' exonuclease activity.

FIG. 10 shows the results of the real-time PCR amplification for the detection of N. meningitidis using TSG primers and a template-dependent DNA polymerase having no 5' to 3' exonuclease activity.

FIG. 11 shows the results of the real-time PCR sensitivity for the detection of S. aureus using a TSG primer and a template-dependent DNA polymerase having no 5' to 3' exonuclease activity.

FIG. 12 shows the results of the signal generation and accumulation from TSG primers depending on a template-dependent nucleic acid polymerase having a 5' to 3' nuclease activity or having no 5' to 3' nuclease activity during nucleic acid synthesis reaction with the repetition of denaturation, hybridization and primer extension.

FIG. 13 shows the results of the real-time PCR amplification for the detection of S. pneumoniae using TSG primers and a template-dependent DNA polymerase having 5' to 3' exonuclease activity.

FIG. 14 shows the results of the real-time PCR amplification for the detection of S. aureus using TSG primers and a template-dependent DNA polymerase having 5' to 3' exonuclease activity.

FIG. 15 shows the results of the real-time PCR amplification for the detection of N. gonorrhoeae using TSG primers and a template-dependent DNA polymerase having 5' to 3' exonuclease activity.

FIG. 16 shows the results of the real-time PCR amplification for the detection of N. meningitidis using TSG primers and a template-dependent DNA polymerase having 5' to 3' exonuclease activity.

FIG. 17 shows the results of the real-time PCR sensitivity for the detection of S. aureus using a TSG primer and a template-dependent DNA polymerase having 5' to 3' exonuclease activity.

DETAILED DESCRIPTION OF THIS INVENTION

The present invention is directed to a novel method for detecting a target nucleic acid sequence in a real-time fashion using a target signal generating primer (TSG primer) with a dual label system and a template-dependent nucleic acid polymerase.

In accordance with the present invention, the dual-labeled primer called a target signal generating primer (TSG primer) with quenching signals is hybridized with a target nucleic acid sequence to induce signal unquenching and extended to synthesize a complementary sequence of the target nucleic acid sequence, finally detecting the signal indicative of the presence of the target nucleic acid sequence. In other words, the TSG primer undergoes both the conformational change for signal unquenching and the 3'-extension reaction.

The present inventors have first found that as a primer without any modified structure such as a hairpin loop structure, the TSG primer could generate target signals by conversion of a quenching state to an unquenching state depending on the hybridization and primer extension. The TSG primers and real-time processes using them have been first proposed by the present inventors.

One of the key advantages of TSG primer is that the extension at the 3'-end of the TSG primer ensures much less variation in signal intensity over change of reaction conditions (e.g., reaction temperatures), leading us to reason that more reliable and stable signal results could be obtained by the extension at the 3'-end of the TSG primer with little or no signal influence upon reaction condition change. Especially, the extension at the 3'-end of the TSG primer enables the TSG primer to amplify the target nucleic acid sequence.

The TSG primer of the present invention in amplification reactions, inter alia, in PCR-based real-time detection methods, is involved in target amplification as well as signal generation, allowing for a successful homogenous assay for target sequences.

Interestingly, the novel real-time PCR detection method of the present invention using the TSG primers works in a distinctly different fashion from conventional real-time PCR approaches, resulting in overcoming drawbacks of conventional technologies and elevating real-time detection efficiency.

The most striking difference of the TSG primer-based method from the conventional probe-based methods such as Molecular beacon and TaqMan probe methods is that the labeled probes are able only to generate target signals not to amplify target sequences, but the TSG primers are able to amplify target sequences as well as to generate target signals. The probe-based methods are compelled to use additional primers for target amplification, which clearly differs from the present invention. It would be recognized by one of skill in the art that conventional methods using labeled probes suffer from probe and primer design, sequence selection and reaction optimization because additional primers for amplification are required. In contrast, since the TSG primer method does not require additional probes, such problems could be minimized.

In addition, since the TSG primers are incorporated into extended or amplified products but the labeled probes are not incorporated into any products, the TSG primer method directly measures amplified products, but the signals from labeled probe method may not be considered to directly reflect amplified products.

Furthermore, the hybridization of labeled probes with target sequences is dependent on concentrations of labeled probes and amplified products, which makes it difficult to perform quantitative analysis. Even though excess labeled probes may be used to improve accuracy of quantitative analysis, they are very likely to produce high background problems. In contrast, the TSG primer method may directly measure target amplification using labeled primers, enabling quantitative analysis of target sequences in much higher accuracy.

In the meantime, several conventional primer-based real-time detection methods such as the Sunrise method and Scorpion method have to form a hairpin structure for quenching fluorescence from them prior to hybridization with target sequences.

However, the utilization of the hairpin structure in the labeled primer-based methods decreases amplification efficiency as well as hybridization efficiency. Moreover, the hairpin structure configured to the labeled primers requires an additional sequence; therefore, the primers have to be designed and prepared by considering both a target complementary sequence and a hairpin-forming sequence. In these contexts, it would be difficult to design the labeled primers with the hairpin structure. In contrast, the TSG primer generates target signals with no help of hairpin structures, and permits to overcome shortcomings associated with hairpin structures.

The Lux method using a single label on primers is different from the present invention using a dual interactive label system on primers in view of a principle mechanism underlying signal generation. The signal from the single label molecule on primers may be affected by various factors such as types of labels, primer sequences around the label, positions of the label on primers and surrounding other components, which is considered as the disadvantages of the Lux method.

As described hereinabove, the TSG primer-based real-time detection method of the present invention has some technical features (particularly, principle of signal generation, structure of oligonucleotides, and function of oligonucleotides) differentiating from conventional primer- and probe-based methods. The technical features of this invention allow for overcoming limitations of conventional real-time methods and detecting target nucleic acid sequences in much more effective manner.

Surprisingly, the present inventors have found that primers hybridized with target nucleic acid sequences undergo a 5'-cleaveage reaction on their 5'-end portion by a template-dependent nucleic acid polymerase having a 5' to 3' nuclease activity and the 5'-cleaveage reaction adopts to detection of target sequences by generating signals for target sequences (see PCT/KR2009/007064).

Where the TSG primer having a reporter or quencher molecule at its 5'-end portion is hybridized with a target sequence (i.e., template), it undergoes the 5'-cleaveage reaction on its 5'-end portion by a template-dependent nucleic acid polymerase having a 5' to 3' nuclease activity and the reporter and quencher molecules are then separated from each other, contributing to signal unquenching on the TSG primer.

It is believed that the proportion of the TSG primers to undergo the 5'-cleavage reaction is varied depending on a 5' to 3' nuclease activity of a template-dependent nucleic acid polymerase, reaction conditions and distance between a reporter molecule and a quencher molecule.

Given that the 5'-cleavage reaction occurs in the present invention when the template-dependent nucleic acid polymerase having the 5' to 3' nuclease activity and the TSG primers having either a reporter or quencher molecule on their 5'-end portion are used, the present invention can give signal indicative of the presence of target nucleic acid sequences in two other fashions: (i) signal generation by signal unquenching of the interactive label system on the TSG primer caused by conformation change upon hybridization with the target nucleic acid sequence; and (ii) signal generation by the 5'-cleaveage reaction on its 5'-end portion of the TSG primer by the template-dependent nucleic acid polymerase having the 5' to 3' nuclease activity.

In the present invention using the template-dependent nucleic acid polymerase having the 5' to 3' nuclease activity, it is preferable that the 5'-cleavage reaction occurs only when the 5'-end portion (more preferably, the 5'-end) of the TSG primer is complementary to the target nucleic acid sequence.

In accordance with the present invention, the target nucleic acid sequences could be detected in a real-time manner with dramatically enhanced efficiency and reliability. To our best knowledge, these scientific findings and technological strategies are first proposed by the present inventors.

In one aspect of the present invention, there is provided a method for detecting a target nucleic acid sequence from a DNA or a mixture of nucleic acids using a target signal generating primer (TSG primer), which comprises the steps of:

(a) hybridizing the target nucleic acid sequence with the TSG primer; wherein the TSG primer comprises (i) a hybridizing nucleotide sequence complementary to the target nucleic acid sequence and (ii) a reporter molecule and a quencher molecule; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase under primer extension conditions such that the 3'-extension reaction is induced at the 3'-end of the TSG primer; and (c) detecting the signal indicative of the presence of the target nucleic acid sequence, whereby the signal indicates the presence of the target nucleic acid sequence in the DNA or the mixture of nucleic acids.

The present inventors have made intensive researches to overcome shortcomings associated with conventional technologies for real-time detection of target nucleic acid sequences. The present inventors have devised novel TSG (target signal generating) primers capable of generating signals depending on hybridization and extension with target nucleic acid sequences, and have in turn constructed various protocols using the primers for detection of target nucleic acid sequences. As results, we have verified that the new protocols or processes exhibit a plausible performance in detection of target nucleic acid sequences, inter alia, real-time detection, and produce signals indicative of the presence of target nucleic acid sequences in both a liquid phase and a solid phase in much stronger and faster manner.

In accordance with the present invention, the TSG primer to be hybridized with the target nucleic acid sequence has an interactive label system containing a reporter molecule and a quencher molecule. Where the TSG primer is not hybridized with the target nucleic acid sequence, the reporter molecule and the quencher molecule on the TSG primer are three-dimensionally adjacent to each other to allow the quencher molecule to quench a signal from the reporter molecule; in contrary, when the TSG primer is hybridized with the target nucleic acid sequence, the reporter molecule and the quencher molecule on the TSG primer are three-dimensionally separated to allow the quencher molecule to unquench the signal from the reporter molecule, whereby the signal indicative of the presence of the target nucleic acid sequence is generated and obtained. As such, the TSG primer has a dual distinct function: (i) signal generation for the target nucleic acid sequence; and (ii) synthesis of a complementary sequence to the target nucleic acid sequence.

Therefore, the primer used in the present invention is called a "Target signal generating primer" (TSG primer) and the present method called "TSG primer Target Detection Assay".

According to the present invention, a target nucleic acid sequence is first hybridized with the TSG primer.

The term used herein "target nucleic acid", "target nucleic acid sequence" or "target sequence" refers to a nucleic acid sequence of interest for detection, which is annealed to or hybridized with a primer under hybridization, annealing or amplifying conditions.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide. The primer of this invention may be comprised of naturally occurring dNMP (i.e., dAMP, dGM, dCMP and dTMP), modified nucleotide, or non-natural nucleotide. The primer may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

There is no intended distinction between the terms "annealing" and "hybridizing", and these terms will be used interchangeably.

The term "TSG primer" used herein means a primer having the abilities of self-quenching and -unquenching and extension. In particular, the TSG primer used in the present invention means a dual-labeled primer capable of both synthesizing a complementary sequence to a target sequence and generating signals indicative of the presence of target nucleic acid sequences in such a manner that where not hybridized with the target nucleic acid sequence, it induces quenching of the interactive label system; where hybridized with the target nucleic acid sequence, it induces unquenching of the interactive label system, generating the signal indicative of the presence of the target nucleic acid sequence.

The term used herein "forward primer" means a primer (5' to 3' direction) complementary to a strand of a target nucleic acid sequence aligned in a 3' to 5' direction. The reverse primer has a complementary sequence to the other strand of the nucleic acid sequence.

The term used herein "three-dimensionally adjacent" in conjunction with the reporter molecule and the quencher molecule on the TSG primer means that the reporter molecule and the quencher molecule are conformationally close to each other without the help of any intramolecular structures of primers such as a hairpin loop.

The TSG primer comprises (i) a hybridizing nucleotide sequence complementary to the target nucleic acid sequence and (ii) a dual interactive label system. The term "complementary" is used herein to mean that primers are sufficiently complementary to hybridize selectively to a target nucleic acid sequence under the designated annealing conditions or stringent conditions, encompassing the terms "substantially complementary" and "perfectly complementary", preferably perfectly complementary.

Alternatively, the TSG primer may further comprise at its 5'-end a non-hybridizing nucleotide sequence non-complementary to the target nucleic acid sequence. Preferably, one of the reporter molecule and the quencher molecule on the TSG primer is located on the non-hybridizing nucleotide sequence and the other is located on the hybridizing nucleotide sequence. The non-hybridizing nucleotide sequence of the TSG primer preferably does not form hairpin-loop structure and does not involve in the formation of an intramolecular structure such as a hairpin-loop. The non-hybridizing nucleotide sequence of the TSG primer preferably carries no restriction site.

Preferably, the TSG primer does not form hairpin-loop structure.

According to a preferred embodiment, the dual label system is positioned on the target complementary sequence of the TSG primer.

According to a preferred embodiment, the 5'-end or a 5'-end portion of the TSG primer has a perfectly complementary sequence to the target nucleic acid sequence.

The TSG primer has the interactive label system containing the reporter molecule and the quencher molecule.

The interactive label system is a signal generating system in which energy is passed non-radioactively between a donor molecule and an acceptor molecule. As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent.

In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

Preferably, the signal indicative of the presence of the target nucleic acid sequence is generated by dual interactive label systems, most preferably the FRET label system.

Where the FRET label is used on the TSG primer, the two labels (the fluorescent reporter molecule and the quencher molecule) are separated from each other to induce signal unquenching when the TSG primer hybridized with the target nucleic acid sequence is in a stretch conformation. When the TSG primer not hybridized with the target nucleic acid sequence is in a twist conformation, the two labels are adjacent to each other to induce signal quenching.

The terms used herein "quenching" and "unquenching" have to be construed in a relative manner. For example, the term "unquenching" may be considered to lower quenching efficiency or level than the term "quenching". In other words, the quenching of signal from the reporter molecule encompasses extinguishment of the signal as well as decrease in signal levels compared to no occurrence of quenching. Furthermore, the unquenching of signal from the reporter molecule encompasses complete recovery of the signal as well as increase in signal levels compared to occurrence of quenching.

The signal indicating the target nucleic acid sequence may be obtained by the differences in signal quenching levels as described above. For instance, where relative fluorescence intensities from the fluorescent reporter molecule are measured to detect the target nucleic acid, the TSG primer not hybridized with the target nucleic acid sequence shows a relative low fluorescence intensity (a quenching state) because the fluorescent reporter molecule and the quencher molecule are spatially (or three-dimensionally) adjacent to each other. Where the TSG primer is hybridized with the target nucleic acid sequence, relatively high fluorescence intensity is detected (an unquenching state) because the fluorescent reporter molecule and the quencher molecule are spatially separated from each other.

The reporter molecule and the quencher molecule may be positioned on any site of the TSG primer so long as the quenching-unquenching switching occurs.

According a preferred embodiment, the reporter molecule and the quencher molecule are positioned at 4-50 nucleotides apart from each other.

According to a preferred embodiment, the reporter molecule and the quencher molecule are positioned at no more than 50 nucleotides, more preferably no more than 40 nucleotides, still more preferably no more than 30 nucleotides, still much more preferably no more than 25 nucleotides apart from each other.

According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

According a preferred embodiment, the reporter molecule or the quencher molecule on the TSG primer is located at its 5'-end or at 1-5 nucleotides apart from its 5'-end. For example, the reporter molecule on the TSG primer is located at its 5'-end or at 1-5 nucleotides apart from its 5'-end and the quencher molecule is located at 4-50 nucleotides apart from the reporter molecule.

According a preferred embodiment, the reporter molecule on the TSG primer is located at its 5'-end or at 1-10 nucleotides apart from its 5'-end, more preferably at its 5'-end.

According a preferred embodiment, the quencher molecule on the TSG primer is located at its 5'-end or at 1-10 nucleotides apart from its 5'-end, more preferably at its 5'-end.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 5464 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671) and Cy5.5 (694). The numeric in parenthesis is a maximum emission wavelength in nanometer.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition, Molecular Probes, Eugene, Oreg., 1996; U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention.

In the FRET label adopted to the TSG primer, the reporter encompasses a donor of FRET and the quencher encompasses the other partner (acceptor) of FRET. For example, a fluorescein dye is used as the reporter and a rhodamine dye as the quencher.

Following the hybridization with the target nucleic acid sequence, the resultant of step (a) is contacted to the template-dependent nucleic acid polymerase under primer extension conditions for extending the TSG primer hybridized with the target nucleic acid sequence.

The phrase "under primer extension conditions" means conditions sufficient to induce the extension reaction at the 3'-end of the TSG primer by a template-dependent nucleic acid polymerase. Such conditions may be conditions for primer extension by conventional nucleic acid polymerases. For example, the conditions will be found in Joseph Sambrook, et al., *Molecular Cloning, A Laboratory Manual*, Cold Spring Harbor Laboratory Press, Cold Spring Harbor, N.Y. (2001). As illustrative example, the conditions include incubation of a target nucleic acid sequence, the TSG primer, a thermostable DNA polymerase (e.g., Taq DNA polymerase), dNTPs and $MgCl_2$ at relatively high temperature (e.g., 50-75° C.) for a suitable period of time.

The extension of the TSG primer is a crucial step for the present invention. Where the extended product is produced by the extension reaction of the TSG primer, it leads to more stable hybridization of the TSG primer sequence incorporated into the extended product with the target nucleic acid sequence. In addition, the extension reaction of the TSG primer permits to incorporate labels on the TSG primer into the extended product, thereby increasing the signal intensity in parallel with the amount of the amplified product. Such coupling phenomenon induced in the present invention ensures more accurate quantitative analysis of the target nucleic acid sequence. In accordance with the present invention, unlikely labeled probes, where the TSG primer per se, is non-specifically hybridized with non-target sequences, any false positive signals may not be generated by performing signal detection under high stringent conditions such as high temperatures (e.g., 50-85° C.). Also, the extension of the TSG primer results in amplification of the target nucleic acid sequence, enabling signal amplification simultaneously with target amplification.

According the present invention, a template-dependent nucleic acid polymerase includes any nucleic acid polymerase known in the art.

One of the prominent advantages of the present invention is to generate target signals even using a template-dependent nucleic acid polymerase without nuclease activities.

According to a preferred embodiment, the template-dependent nucleic acid polymerase used in the present invention has no nuclease activity.

According to a preferred embodiment, the template-dependent nucleic acid polymerase used in the present invention has no 5' to 3' nuclease activity The template-dependent nucleic acid polymerase capable of being used in the present invention may include any nucleic acid polymerases, for example, Klenow fragment of *E. coli* DNA polymerase I, a thermostable DNA polymerase and bacteriophage 17 DNA polymerase. Preferably, the polymerase is a thermostable DNA polymerase which may be obtained from a variety of bacterial species.

According to a preferred embodiment, where the template-dependent nucleic acid polymerase used in the present invention has a 5' to 3' nuclease activity, the TSG primer is extended at its 3'-end by the polymerase activity of the template-dependent nucleic acid polymerase and cleaved at its 5'-end by the 5' to 3' nuclease activity of the template-dependent nucleic acid polymerase, so that either the reporter molecule or the quencher molecule is released to generate the signal indicative of the presence of the target nucleic acid sequence.

Preferably, the template-dependent nucleic acid polymerase having the 5' to 3' nuclease activity is a thermostable DNA polymerase which may be obtained from a variety of bacterial species, including *Thermus aquaticus* (Taq), *Thermus thermophilus, Thermus filiformis, Thermus flavus, Thermus antranikianii, Thermus caldophilus, Thermus chliarophilus, Thermus igniterrae, Thermus lacteus, Thermus oshimai, Thermus ruber, Thermus rubens, Thermus scotoductus, Thermus silvanus, Thermus* species Z05 and *Thermus* species sps 17. Most preferably, the template-dependent nucleic acid polymerase having the 5' to 3' nuclease activity is Taq DNA polymerase.

Interestingly, the present inventors have found that the TSG primer hybridized with target nucleic acid sequences are extended at its 3'-end and also cleaved on its 5'-end portion (e.g., 5'-end) by only contacting to template-dependent nucleic acid polymerases having the 5' to 3' nuclease activity. The cleavage reaction on the 5'-end portion of the TSG primer is also responsible for signal generation in the present invention.

In summary, where the present invention is performed to involve the 5'-cleave reaction of the TSG primer, the present invention can give signal indicative of the presence of target nucleic acid sequences in two other fashions: (i) signal generation by signal unquenching of the interactive label system on the TSG primer caused by conformation change upon hybridization with the target nucleic acid sequence; and (ii) signal generation by the 5'-cleaveage reaction on its 5'-end portion of the TSG primer by the template-dependent nucleic acid polymerase having the 5' to 3' nuclease activity.

According to a preferred embodiment, the TSG primer comprises a match sequence to the target nucleic acid sequence at its 5'-end or on its 5'-end portion.

The term used herein "5'-end portion" in conjunction with the TSG primer refers to a portion or region comprising any lengthy consecutive sequence from the 5'-end of the TSG primer. Preferably, the 5'-end portion of the TSG primer has the 5'-end and a sequence comprising 1-10 nucleotides (more preferably 1-7 nucleotides, still more preferably 1-5 nucleotides, still much more preferably 1-3 nucleotides) apart from the 5'-end.

Alternatively, the template-dependent nucleic acid polymerase having a 3' to 5' exonuclease activity can be used in the present invention.

According to a preferred embodiment, where the template-dependent nucleic acid polymerase having the 3' to 5' exonuclease activity is used, the TSG primer comprises at least one mismatch nucleotide sequence at its 3'-end portion or 3'-end.

According to a preferred embodiment, where the TSG primer comprises at least one mismatch nucleotide sequence at its 3'-end portion or 3'-end, the mismatch nucleotide sequence has no label.

The number of the mismatch nucleotides may be 1-5, preferably 1-4, more preferably 1-3, still more preferably 1-2 and most preferably 1. Where primers carry at least 2 mismatch nucleotides, the mismatch nucleotides may be located continuously or intermittently.

According to a preferred embodiment, According to a preferred embodiment, where the template-dependent nucleic acid polymerase having the 3' to 5' exonuclease activity is used, the TSG primer has at least one mismatch nucleotide having a backbone resistant to the 3' to 5' nuclease activity of template-dependent nucleic acid polymerases at its 3'-end portion.

According to a preferred embodiment, where the template-dependent nucleic acid polymerase having the 3' to 5' exonuclease activity is used, the TGS primer comprises at its 3'-end a single match-determinant nucleotide having a backbone resistant to the 3' to 5' nuclease activity of template-dependent nucleic acid polymerases.

The single match-determinant nucleotide at the 3'-end of the TSG primer forms a base pair only when it is hybridized with a match nucleotide present on the opposed strand. However, the single match-determinant nucleotide of the TSG primer can not form the base pair when a nucleotide present on the opposed strand is not complementary to the single match-determinant nucleotide.

In the present invention, because the single match-determinant nucleotide at the 3'-end of the TSG primer contains a backbone resistant to the 3' to 5' nuclease activity, a cleavage reaction is not induced even when the 3'-end of the TSG primer is not base-paired, thereby inducing no extension reaction.

The extension of the TSG primer gives rise to higher stable hybridization with target sequences compared with no extended TSG primer. Therefore, with adjusting temperatures, the presence of the extended product (i.e., target sequence) can be detected by analyzing changes in signals.

Preferably, the present invention is used for detection of nucleotide variations. More preferably, the nucleotide variation detected in this invention is a base substitution, furthermore preferably, SNP (single nucleotide polymorphism) and point mutation.

According to a preferred embodiment, nucleotide variations can be positioned at opposite to the single match-determinant nucleotide at the 3'-end of the TSG primer.

The backbone resistant to the 3' to 5' nuclease activity includes any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 3' to 5' nuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

According to a preferred embodiment, the template-dependent nucleic acid polymerase with the 3' to 5' exonuclease activity is a thermostable DNA polymerase which may be obtained from a variety of bacterial species, including *Thermococcus litoralis, Thermococcus barossi, Thermococcus gorgonarius, Thermotoga maritima, Thermotoga neapolitana, Thermosipho africanus, Pyrococcus furiosus* (Pfu), *Pyrococcus woesei; Pyrococcus horikoshii, Pyrococcus abyssi, Pyrodictium occultum, Aquifex pyrophilus* and *Aquifex aeolieus*. Most preferably, the template-dependent nucleic acid polymerase having the 3' to 5' nuclease activity is Pfu DNA polymerase.

According to a preferred embodiment, the present invention further comprises repeating the steps (a)-(b) or (a)-(c) with denaturation between repeating cycles at least twice to amplify the signal indicative of the presence of the target nucleic acid sequence. The number of the cycle repetition is not particularly limited, typically at least two, preferably at least five, more preferably at least ten. The denaturation is to render the double stranded duplexes formed in step (a) into single stranded nucleic acids. Methods for denaturation includes, but not limited to, heating, alkali, formamide, urea and glycoxal treatment, enzymatic methods (e.g., helicase action) and binding proteins. For instance, the denaturation may be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

Finally, the signal indicative of the presence of the target nucleic acid sequence is detected. The signal detection may be performed for each cycle of the repetition (i.e., real-time manner), at the end of the repetition (i.e., end-point manner) or at each of predetermined time intervals during the repetition. Preferably, the signal detection may be performed for each cycle of the repetition to improve the detection accuracy.

The signal may be detected or measured by conventional methods for each label. For example, the fluorescence signal may be detected or measured by conventional methods, e.g., fluorometers.

The advantages of the present invention become evident in the signal detection step. Where the signal detection is carried out under high stringent conditions such as high temperatures (e.g., 50-85° C.), false positive signals owing to hybridization of TSG primer with non-target nucleic acid sequences may be completely eliminated.

According to a preferred embodiment, the signal detection is performed by measuring or analyzing signal change from the reporter molecule of the label system composed of the reporter and quencher molecules.

According to a preferred embodiment, where the quencher molecule is fluorescent, the signal detection is performed by measuring signal change from the quencher molecule or signal changes from both the quencher molecule and the reporter molecule.

According to a preferred embodiment, the quencher molecule is fluorescent and the signal indicative of the presence of the target nucleic acid sequence to be detected is a signal from the fluorescent quencher molecule.

One of the prominent features of the present invention is to successfully obtain signals in both a liquid phase and a solid phase. The present invention can be carried out in two phases, i.e., a liquid phase and a solid phase.

I. Target Detection in a Liquid Phase

1. Target Detection Using TSG Primer and Nucleic Acid Polymerase

In accordance with the first protocol, the target nucleic acid sequence is detected using the TSG primer and the template-dependent nucleic acid polymerase (see FIGS. 1A and 1B).

The first protocol comprises the steps of:

(a) hybridizing the target nucleic acid sequence with the TSG primer; wherein the TSG primer comprises (i) a hybridizing nucleotide sequence complementary to the target nucleic acid sequence and (ii) a reporter molecule and a quencher molecule; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase under primer extension conditions such that the 3'-extension reaction is induced at the 3'-end of the TSG primer; and (c) detecting the signal indicative of the presence of the target nucleic acid sequence, whereby the signal indicates the presence of the target nucleic acid sequence in the DNA or the mixture of nucleic acids.

According to a preferred embodiment, the detection of step (c) is performed in a real-time manner, an end-point manner, or a predetermined time interval manner.

2. Target Detection Using TSG Primer and Nucleic Acid Polymerase Having the 5' to 3' Nuclease Activity In accordance with the second protocol, the target nucleic acid sequence is detected using the TSG primer and the template-dependent nucleic acid polymerase having the 5' to 3' nuclease activity.

Preferably, the second protocol comprises the steps of:

(a) hybridizing the target nucleic acid sequence with the TSG primer; wherein the TSG primer comprises (i) a hybridizing nucleotide sequence complementary to the target nucleic acid sequence and (ii) a reporter molecule and a quencher molecule; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase having a 5' to 3' nuclease activity under primer extension and cleavage conditions such that the 3'-extension reaction at the 3'-end of the TSG primer and the 5'-cleavage reaction on the 5'-end portion of the TSG primer are induced, whereby either the reporter molecule or the quencher molecule is released from the TSG primer to generate the signal indicative of the presence of the target nucleic acid sequence; and (c) detecting the signal indicative of the presence of the target nucleic acid sequence, whereby the signal indicates the presence of the target nucleic acid sequence in the DNA or the mixture of nucleic acids.

According to a preferred embodiment, the present invention further comprises repeating the steps (a)-(b) or (a)-(c) with denaturation between repeating cycles at least twice to amplify the signal indicative of the presence of the target nucleic acid sequence.

According to a preferred embodiment, the detection of step (c) is performed in a real-time manner, an end-point manner, or a predetermined time interval manner.

3. Target Detection Using TSG Primer, Counterpart Primer and Nucleic Acid Polymerase The third protocol of the present invention detects the target nucleic acid sequence by use of (i) a template-dependent nucleic acid polymerase and (ii) a primer pair composed of the TSG primer and its counterpart primer capable of amplifying the target nucleic acid sequence, such that the signal indicative of the presence of the target nucleic acid sequence is amplified simultaneously with the target amplification (see FIGS. 2A and 2B).

The counterpart primer may be used as a TSG primer or not.

Preferably, the third protocol detects the target nucleic acid sequence in the DNA or the mixture of nucleic acids through amplification reactions using the TSG primer, comprising the steps of:

(a) hybridizing the target nucleic acid sequence with a primer pair composed of two primers as a forward primer and a reverse primer capable of amplifying the target nucleic acid sequence; wherein at least one of the two primers is the TSG primer; wherein the TSG primer comprises (i) a hybridizing nucleotide sequence complementary to the target nucleic acid sequence and (ii) a reporter molecule and a quencher molecule; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase under primer extension conditions such that the 3'-extension reaction at the 3'-ends of the two primers is induced;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal indicates the presence of the target nucleic acid sequence.

4. Target Detection Using TSG Primer, Counterpart Primer and Nucleic Acid Polymerase Having the 5' to 3' Nuclease Activity The fourth protocol of the present invention detects the target nucleic acid sequence by use of (i) a template-dependent nucleic acid polymerase having the 5' to 3' nuclease activity and (ii) a primer pair composed of the TSG primer and its counterpart primer capable of amplifying the target nucleic acid sequence, such that the signal indicative of the presence of the target nucleic acid sequence is amplified simultaneously with the target amplification (see FIGS. 3A and 3B).

Preferably, the fourth protocol comprises the steps of:

(a) hybridizing the target nucleic acid sequence with a primer pair composed of two primers as a forward primer and a reverse primer capable of amplifying the target nucleic acid sequence; wherein at least one of the two primers is the TSG primer; wherein the TSG primer comprises (i) a hybridizing nucleotide sequence complementary to the target nucleic acid sequence and (ii) a reporter molecule and a quencher molecule; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase under primer extension and cleavage conditions such that the 3'-extension reaction at the 3'-end of the TSG primer and the 5'-cleavage reaction on the 5'-end portion of the TSG primer are induced, whereby either the reporter molecule or the quencher molecule of the TSG primer is released from the TSG primer to generate the signal indicative of the presence of the target nucleic acid sequence; and (c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal indicates the presence of the target nucleic acid sequence.

II. Target Detection in a Solid Phase

The prominent advantage of the present invention is to be effective in detection of target nucleic acid sequences even in a solid phase such as microarray.

According to a preferred embodiment, the present invention is performed on the solid phase and the TSG primer is immobilized on the surface of a solid substrate through its 5'-end.

1. On-Chip Target Detection Using TSG Primer and Nucleic Acid Polymerase

In accordance with the first solid protocol, the target nucleic acid sequence is detected using the TSG primer and a template-dependent nucleic acid polymerase on the solid phase (see FIGS. 4A and 4B).

Preferably, the first solid protocol comprises the steps of:

(a) hybridizing the target nucleic acid sequence with the TSG primer; wherein the TSG primer comprises (i) a hybridizing nucleotide sequence complementary to the target nucleic acid sequence and (ii) a reporter molecule and a quencher molecule; wherein the TSG primer is immobilized on the surface of a solid substrate through its 5'-end; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase under primer extension conditions such that the 3'-extension reaction at the 3'-end of the TSG primer is induced; and (c) detecting the signal indicative of the presence of the target nucleic acid sequence on the solid substrate, whereby the signal indicates the presence of the target nucleic acid sequence in the DNA or the mixture of nucleic acids.

2. On-Chip Target Detection Using TSG Primer, Counterpart Primer and Nucleic Acid Polymerase The second solid protocol of the present invention detects the target nucleic acid sequence by use of (i) a template-dependent nucleic acid polymerase and (ii) a primer pair composed of the TSG primer and its counterpart primer capable of amplifying the target nucleic acid sequence, such that the signal indicative of the presence of the target nucleic acid sequence is amplified simultaneously with the target amplification.

In other words, the second solid protocol realizes on-chip real-time PCR technology.

Preferably, the second solid protocol comprises the steps of:

(a) hybridizing the target nucleic acid sequence with a primer pair composed of two primers as a forward primer and a reverse primer capable of amplifying the target nucleic acid sequence; wherein at least one of the two primers is the TSG primer; wherein the TSG primer comprises (i) a hybridizing nucleotide sequence complementary to the target nucleic acid sequence and (ii) a reporter molecule and a quencher molecule; wherein at least one of the two primers is immobilized on the surface of a solid substrate through its 5'-end and the immobilized primer is the TSG primer; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained;

(b) contacting the resultant of step (a) to a template-dependent nucleic acid polymerase under primer extension conditions such that the 3'-extension reaction at the 3'-ends of the two primers is induced;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal indicates the presence of the target nucleic acid sequence.

According to a preferred embodiment, the TSG primer is immobilized on the surface of a solid substrate through its 5'-end, and the other primer is not immobilized and not a TSG primer.

According to a preferred embodiment, the TSG primer and the counterpart primer have a dual priming oligonucleotide (DPO) structure represented by the following general formula I:

$$5'\text{-}X_P\text{-}Y_q\text{-}Z_r\text{-}3' \qquad (I)$$

wherein, $X_p$ represents a 5'-first priming portion having a hybridizing nucleotide sequence complementary to the target nucleic acid; $Y_q$ represents a separation portion comprising at least three universal bases, $Z_r$ represents a 3'-second priming portion having a hybridizing nucleotide sequence complementary to the target nucleic acid; p, q and r represent the number of nucleotides, and X, Y, and Z are deoxyribonucleotides or ribonucleotides; the $T_m$ of the 5'-first priming portion is higher than that of the 3'-second priming portion and the separation portion has the lowest $T_m$ in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the primer is enhanced.

The DPO structure as a primer version of DSO (dual specificity oligonucleotide) was first proposed by the present inventor (see WO 2006/095981; Chun et al., Dual priming oligonucleotide system for the multiplex detection of respiratory viruses and SNP genotyping of CYP2C19 gene, *Nucleic Acid Research*, 35: 6e40(2007)).

The DPO embodies a novel concept in which its hybridization or annealing is dually determined by the 5'-high $T_m$ specificity portion (or the 5'-first priming portion) and the 3'-low $T_m$ specificity portion (or the 3'-second priming portion) separated by the separation portion, exhibiting dramatically enhanced hybridization specificity (see WO 2006/095981; Kim et al., Direct detection of lamivudine-resistant hepatitis B virus mutants by multiplex PCR using dual-priming oligonucleotide primers, *Journal of Virological Methods*, 149:76-84 (2008); Kim, et. al., Rapid detection and identification of 12 respiratory viruses using a dual priming oligonucleotide system-based multiplex PCR assay, Journal of Virological Methods, doi:10.1016/j.jviromet.2008.11.007 (2008); Horii et. al., Use of dual priming oligonucleotide system to detect multiplex sexually transmitted pathogens in clinical specimens, Letters in Applied Microbiology, doi:10.111/j.1472-765×2009.02618x (2009)). As such, the DPO has eventually two primer segments with distinct hybridization properties: the 5'-first priming portion that initiates stable hybridization, and the 3'-second priming portion that mainly determines target specificity.

The amplification (particularly, multiplex amplification) using primers having the DPO structure in the present invention ensures to obtain amplicons without false positive and negative data.

According to a preferred embodiment, the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof. More preferably, the universal base is deoxyinosine, 1-(2'-deoxy-beta-D-ribofuranosyl)-3-nitropyrrole or 5-nitroindole, most preferably, deoxyinosine.

Preferably, the separation portion comprises contiguous nucleotides having at least three, more preferably at least four, most preferably at least five universal bases.

Preferably, in the DPO structure the 5'-first priming portion is longer than the 3'-second priming portion. The 5'-first priming portion is preferably 15-60 nucleotides, more preferably 15-40 nucleotides, still more preferably 15-25 nucleotides in length. It is preferable that the 3'-second priming portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length. According to a preferred embodiment, the $T_m$ of the 5'-first priming portion ranges from 40° C. to 80° C., more preferably 45° C. to 65° C. The $T_m$ of the 3'-second priming portion ranges preferably from 10° C. to 40° C. It is preferable that the $T_m$ of the separation portion ranges from 3° C. to 15° C.

According to a preferred embodiment, the $T_m$ of the 3'-first priming portion ranges from 40° C. to 80° C., more preferably 45° C. to 65° C. The $T_m$ of the 5'-second priming portion ranges preferably from 10° C. to 40° C. It is preferable that the $T_m$ of the separation portion ranges from 3° C. to 15° C.

According to a preferred embodiment, all of the two primers used in the amplification for the present invention have the DPO structure.

The conventional technologies using primers for detecting target nucleic acid cannot be free from false signals at a satisfactory level due to inherent limitations of primers and probes used. However, the primers having the DPO structure with such deliberative design are hybridized with the target nucleic acid sequence with a dramatically enhanced specificity, permitting to detect the target nucleic acid sequence with no false signals.

As used herein, the term "conventional" in conjunction with primers means any primer not having DPO structure. They are described herein as conventional primers.

According to a preferred embodiment, one of the reporter molecule and the quencher molecule is positioned on the 5'-first priming portion and the other on the 5'-first priming portion, 3'-second priming portion or separation portion.

The present invention does not require any particular sequence or length of the target nucleic acid sequences to be detected and/or amplified.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988)). For reverse transcription, a random hexamer or an oligonucleotide dT primer hybridizable to mRNA can be used.

The oligonucleotide dT primer is comprised of dTMPs, one or more of which may be replaced with other dNMPs so long as the dT primer can serve as primer. Reverse transcription can be done with reverse transcriptase that has RNase H activity. If one uses an enzyme having RNase H activity, it may be possible to omit a separate RNase H digestion step by carefully choosing the reaction conditions.

In particular, target nucleic acid sequences which may be detected and/or amplified include any naturally occurring procaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The advantages of the present invention may be highlighted in the simultaneous (multiplex) detection of at least two target nucleic acid sequences.

According to a preferred embodiment, the target nucleic acid sequence comprises at least two types (more preferably, at least three types, still more preferably at least five types) of nucleic acid sequences and the TSG primers comprises at least two types (more preferably, at least three types, still more preferably at least five types) of primers. According to a preferred embodiment, the counterpart primer capable of amplifying the target nucleic acid sequence together with the TSG primer comprises at least two types (more preferably, at least three types, still more preferably at least five types) of primers.

For example, where the present invention is performed using a reaction vessel containing five TSG primers (each having a fluorescent reporter molecule with different emission wavelength), five counterpart primers and a nucleic acid sample, it generates five different fluorescence signals corresponding to five different target nucleic acids, permitting the simultaneous detection of the five different target nucleic acid sequences in a real-time manner. In this case, all of quencher molecules used may be selected to have different properties from each other. Alternatively, all or some of quencher molecules used may be selected to have the same properties.

Furthermore, the present invention is very useful in detection of a nucleotide variation. The term "nucleotide variation" used herein refers to a nucleotide polymorphism in a DNA sequence at a particular location among contiguous DNA segments that are otherwise similar in sequence. Such contiguous DNA segments include a gene or any other portion of a chromosome. For example, the nucleotide variation detected in the present invention includes SNP (single nucleotide polymorphism), deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations.

According to a preferred embodiment, the target nucleic acid sequence used in the present invention is a pre-amplified nucleic acid sequence. The utilization of the pre-amplified nucleic acid sequence permits to significantly increase the sensitivity and specificity of target detection of the present invention. The target nucleotide sequence in a smaller amount is pre-amplified to give a suitable amount and then detected by the present method, elevating the sensitivity and specificity of target detection of the present invention. Interestingly, where the TSG primer to be hybridized with a sequence downstream of primers used in the pre-amplification is used in the present method, it serves as a nested primer to increase the specificity of target detection of the present invention.

According to a preferred embodiment, where the pre-amplified nucleic acid sequence is used in the present invention to detect target nucleic acid sequences by amplification reaction, the primer pair used in the present invention is a primer pair for a nested amplification.

In another aspect of this invention, there is provided a kit for detecting a target nucleic acid sequence from a DNA or a mixture of nucleic acids using a target signal generating primer (TSG primer), which comprises:

(a) the TSG primer comprising (i) a hybridizing nucleotide sequence complementary to the target nucleic acid sequence and (ii) a reporter molecule and a quencher molecule; wherein when the TSG primer is not hybridized with the target nucleic acid sequence, the reporter molecule and the quencher molecule are three-dimensionally adjacent to each other to allow the quencher molecule to quench a signal from the reporter molecule; wherein when the TSG primer is hybridized with the target nucleic acid sequence, the reporter molecule and the quencher molecule are three-dimensionally separated to allow the quencher molecule to unquench the signal from the reporter molecule, whereby the signal indicative of the presence of the target nucleic acid sequence is generated and obtained; and (b) a template-dependent nucleic acid polymerase capable of inducing the 3'-extension reaction at the 3'-end of the TSG primer by acting on a hybridization resultant between the TSG primer and the target nucleic acid sequence.

Since the kit of this invention is constructed to perform the detection method of the present invention described above, the common descriptions between them are omitted in order to avoid undue redundancy leading to the complexity of this specification.

The present kits may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity.

The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents afore-described in separate packaging or compartments.

The features and advantages of the present invention will be summarized as follows:

(a) The present invention is drawn to a novel real-time PCR method for detecting a target nucleic acid sequence. The TSG primer is capable of generating signals indicative of the presence of target nucleic acid sequence from the dual interactive label system and amplifying target nucleic acid sequence by its 3'-extension reaction during PCR reaction. Accordingly, it could be appreciated that the present invention may provide a novel method to detect target nucleic acid sequences simultaneously with target amplification in a real-time PCR manner.

(b) The extension reaction of the TSG primer permits to incorporate the dual labeled TSG primer into the extended product, thereby generating the signal intensity in parallel with the amount of the amplified product. Such coupling strategy adopted to the present invention ensures more accurate quantitative analysis of target nucleic acid sequences.

(c) Unlikely labeled probes, where the TSG primer per se, is non-specifically hybridized with non-target sequences without any primer extension, false positive signals may not be generated by performing signal detection under high stringent conditions such as high temperature.

(d) The signal generation in the present invention can be accomplished only by hybridization with target nucleic acid sequences without cleavage reactions by nuclease activities. In this connection, the present invention necessarily does not require that nucleic acid polymerases should have the 5' to 3' nuclease activity or 3' to 5' nuclease activity and thus enables to use a wide variety of nucleic acid polymerases for diverse applications.

(e) Where using nucleic acid polymerases having the 5' to 3' nuclease activity, the present invention can obtain signals from the 5'-cleavage reaction of the TSG primer hybridized with target nucleic acid sequences, increasing target detection efficiency.

(f) The conventional real-time PCR methods require labeled probes or complicatedly modified primer structure such as a hairpin structure, which makes the design, synthesis or sequence selection of the probe and primer difficult.

However, since the TSG primer of the present invention is used for not only target amplification but also signal amplification without additional labeled probes or complicatedly modified primer structure, its design, synthesis and sequence selection for real-time PCR is very simple and easy. Therefore, the present invention provides a novel real-time PCR method which can be executed in much more convenient manner than conventional real-time PCR technologies.

(g) Optimization of conventional probe-based real-time PCR methods is difficult because it is necessary that hybridization conditions should be optimized for probes as well as primers. Conventional real-time PCR methods using primers with tails to form hairpin loops are supposed to optimize reaction conditions with considering formation and deformation of hairpin loops in primers. In contrast, the present invention could be completely free from the troublesome matters and shortcomings associated with the optimization of such conventional real-time PCR methods because its optimization may be made with regard only to primers without any structural modification.

(h) The conventional real-time PCR methods are unlikely to adopt to a multiplex assay due to difficulties in primer or probe design and optimization. In contrast, since the present invention uses only a labeled primer without additional probes or complicatedly modified primer structure in real-time PCR, it is possible to exhibit excellent real-time target detection in a multiplex manner.

(i) Compared to the conventional real-time PCR probes, the TSG primer is extended during the process and the extended TSG primer shows higher binding strength to target nucleic acid sequences. The conventional real-time PCR primers require a complicatedly modified structure such as a hairpin loop which bothers the binding to the target nucleic acid sequence. In contrast, the TSG primer does not require such modifications so that the TSG primer has better binding efficiency to target nucleic acid sequences. This feature is responsible in part for enhancing the target detection efficiency of the present method.

(j) The present method can readily realize a real-time PCR reaction by simply labeling the primers that are designed to be used for conventional PCR reactions and applying the labeled primers as TSG primers to the real-time PCR reaction. In short, primers to generate amplicons in conventional PCR reactions are easily labeled with suitable labels and then used to detect target nucleic acid sequences in the present invention by real-time PCR reactions. In this regard, the present method is considered to be time- and cost-effective in the development of a real-time PCR assay.

(k) As discussed hereinabove, the primers used in the present invention having the DPO structure gives rise to the improvement in its binding specificity, thereby eliminating false positive signals associated with non-target binding of primers in real-time PCR reactions.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of the TSG Primer with DNA Polymerase Having No 5' to 3' Exonuclease Activity in the Detection of Target Nucleic Acid Sequences The TSG primer of this invention was evaluated whether the TSG primer can generate a signal sufficient to detect a target nucleic acid sequence only by its target hybridization and extension wherein a template-dependent nucleic acid polymerase without 5' to 3' exonuclease activity is used.

To test this evaluation, we used *Streptococcus. pneumoniae* gene or *Staphylococcus. aureus* gene as target templates. For experimental convenience, the synthetic oligonucleotides were used as templates for *S. pneumoniae* gene and *S. aureus* gene. Stoffel Fragment lacking intrinsic 5' to 3' exonuclease activity was used as the DNA polymerase. Two TSG primers having different distances between a reporter molecule and a quencher molecule were examined respectively for each target. 6-FAM (6-carboxyfluoresceine) was used as a fluorescent reporter molecule and located at 5'-end of TSG primers. Black Hole quencher 1 (BHQ-1) was used as a quencher molecule. Nucleic acid synthesis reaction was conducted without the repetition of denaturation, hybridization and primer extension. The signals were measured at a predetermined time interval.

A. Nucleic Acid Synthesis Reaction for the Detection of *S. pneumoniae* Gene

When the target nucleic acid sequence of the *S. pneumoniae* gene is used as a template, the sequences of the synthetic template and the TSG primers used in this Example are:

SP_T105
(SEQ ID NO: 1)
5'-TTACTGAAAGACAATGAAGACAACCTAACAGGGGAAGATGTTCGCG

AAGGCTTAACTGCAGTTATCTCAGTTAAACACCCAAATCCACAGTTTGA

AGGACAAACC-3'

SP_TSG(9)
(SEQ ID NO: 2)
5'-[6-FAM]TCCTTCAAAC[T(BHQ-1)]GTGGATTTGGGTGT-3'

SP_TSG(21)
(SEQ ID NO: 3)
5'-[6-FAM]TCCTTCAAACTGTGGATTTGGG[T(BHQ-1)]GT-3'

(The number 9 or 21 in the parenthesis means the distance of nucleotides between a reporter molecule and a quencher molecule)

The nucleic acid synthesis reaction with the TSG primer was conducted in the final volume of 20 µl containing 2 pmole of template (SEQ ID NO: 1), 2 µl of 10× Stoffel buffer [containing 100 mM Tris-HCl (pH 8.3) and 100 mM KCl], 1 unit of AmpliTaq® DNA polymerase, Stoffel Fragment (Applied BioSystems, USA), 200 µM each of four dNTPs (dATP, dCTP, dGTP and dTTP), 5 mM of $MgCl_2$ and 5 pmole of the TSG primer (SEQ ID NO: 2 or 3); the tube containing the reaction mixture was placed in the real-time thermocycler (CFX96, Bio-Rad); the reaction mixture was denatured for 2 min at 95° C. and subjected to incubation for 40 min at 50° C. Detection of the generated signal was performed at the interval of 1 min.

As represented in FIG. 5, each of two TSG primers showed much higher fluorescent intensity in the presence of the template (Nos. 1 and 3) than that in the absence of the template (Nos. 2 and 4). Therefore, it could be understood that the TSG primers can provide signals sufficient for detecting *S. pneumoniae* gene through the hybridization and extension of the TSG primers during the nucleic acid synthesis reaction.

It is noteworthy that the TSG primer (SEQ ID NO: 3) having a reporter molecule at 21 nucleotides apart from a quencher molecule showed more distinct changes of signal intensity (i.e., change in RFU values) in the presence and absence of the template than the TSG primer (SEQ ID NO: 2) having a reporter molecule at 9 nucleotides apart from a quencher molecule.

B. Nucleic Acid Synthesis Reaction for the Detection of *S. aureus* Gene

When the target nucleic acid sequence of the *S. aureus* gene is used as a template, the sequences of the synthetic template and the TSG primers used in this Example are:

```
SA_T200
                                            (SEQ ID NO: 4)
5'-GCCAATAAAACTAGGAGGAAATTTAAATGTTAGAATTTGAACAAGG

ATTTAATCATTTAGCGACTTTAAAGGTCATTGGTGTAGGTGGTGGCGGT

AACAACGCCGTAAACCGAATGATTGACCACGGAATGAATAATGTTGAAT

TTATCGCTATCAACACAGACGGTCAAGCTTTAAACTTATCTAAAGCTGA

ATCTAAA-3'

SA_TSG(6)
                                            (SEQ ID NO: 5)
5'-[6-FAM]CATTCCG[T(BHQ-1)]GGTCAATCATTCGGTT-3'

SA_TSG(21)
                                            (SEQ ID NO: 6)
5'-[6-FAM]CATTCCGTGGTCAATCATTCGG[T(BHQ-1)]T-3'
```

(The number 6 or 21 in the parenthesis means the distance of nucleotides between a reporter molecule and a quencher molecule)

The nucleic acid synthesis reaction was conducted as the protocol used for *S. pneumoniae*, except for template (0.2 pmole of *S. aureus*) and TSG primers (SEQ ID NO: 5 or 6).

As represented in FIG. 6, each of two TSG primers showed much higher fluorescent intensity in the presence of the template (Nos. 1 and 3) than that in the absence of the template (Nos. 2 and 4). Therefore, it could be appreciated that the TSG primers can provide signals sufficient for detecting *S. aureus* gene through the hybridization and extension of the TSG primers during the nucleic acid synthesis reaction.

It is noteworthy that the TSG primer (SEQ ID NO: 6) having a reporter molecule at 21 nucleotides apart from a quencher molecule showed more distinct changes of signal intensity (i.e., change in RFU values) in the presence and absence of the template than the TSG primer (SEQ ID NO: 5) having a reporter molecule at 6 nucleotides apart from a quencher molecule.

Example 2: Examination of the TSG Primer with DNA Polymerase Having No 5' to 3' Exonuclease Activity Under the Conditions of Real-Time PCR Reaction for the Detection of a Target Nucleic Acid We further examined whether the TSG primer can generate a signal sufficient to detect a target nucleic acid sequence during real-time PCR reaction using a template-dependent nucleic acid polymerase without 5' to 3' exonuclease activity.

To examine this evaluation, real-time PCR reactions for the detection of *S. pneumoniae*, *S. aureus*, *Neisseria gonorrhoeae* and *Neisseria meningitidis* genes were conducted respectively using primer pairs including TSG primers. Stoffel Fragment lacking intrinsic 5' to 3' exonuclease activity was used as a DNA polymerase. Two TSG primers having different distances between a reporter molecule and a quencher molecule were examined for each target gene.

A. Real-Time PCR for the Detection of *S. pneumoniae* Gene

When the target nucleic acid sequence of the *S. pneumoniae* gene is used as a template, the sequences of a forward primer and TSG primers (as reverse primers) used in this Example are:

```
SP_F1
                                            (SEQ ID NO: 7)
5'-GGTTTCCGTACAGCCTTGAIIIIIGTTATCAATG-3'

SP_TSG(9)
                                            (SEQ ID NO: 2)
5'-[6-FAM]TCCTTCAAAC[T(BHQ-1)]GTGGATTTGGGTGT-3'

SP_TSG(21)
                                            (SEQ ID NO: 3)
5'-[6-FAM]TCCTTCAAACTGTGGATTTGGG[T(BHQ-1)]GT-3'
```

(I represents deoxyinosine and the number 9 or 21 in the parenthesis means the distance of nucleotides between a reporter molecule and a quencher molecule)

The real-time PCR reaction for the detection of *S. pneumoniae* was conducted in the final volume of 20 μl containing 10 ng of genomic DNA of *S. pneumoniae*, 2 μl of 10× Stoffel buffer containing 100 mM Tris-HCl (pH 8.3) and 100 mM KCl, 1 unit of AmpliTaq® DNA polymerase, Stoffel Fragment (Applied BioSystems, USA), 200 μM each of four dNTPs (dATP, dCTP, dGTP and dTTP), 5 mM of MgCl$_2$, 5 pmole of forward primer (SEQ ID NO: 7) and 5 pmole of TSG primer (SEQ ID NO: 2 or 3) as a reverse primer; the tube containing the reaction mixture was placed in the real-time thermocycler (CFX96, Bio-Rad); the reaction mixture was denatured for 2 min at 95° C. and subjected to 30 cycles of 30 s at 94° C., 60 s at 55° C. and 10 s at 72° C. Detection of the generated signal was performed at the annealing step (55° C.) of each cycle.

As shown in FIG. 7, fluorescent signals for *S. pneumoniae* were observed in the presence of *S. pneumoniae* template (Nos. 1 and 3) in the real-time PCR reaction using TSG primers and a template-dependent DNA polymerase having no 5' to 3' nuclease activity, whereas there was no fluorescent signal in the negative controls without the target template (Nos. 2 and 4).

The TSG primer (SEQ ID NO: 3) having a reporter molecule at 21 nucleotides apart from a quencher molecule showed lower Ct values and higher RFU values than the TSG primer (SEQ ID NO: 2) having a reporter molecule at 9 nucleotides apart from a quencher molecule.

B. Real-Time PCR for the Detection of *S. aureus* Gene

When the target nucleic acid sequence of the *S. aureus* is used as a template, the sequences of a forward primer and TSG primers (as reverse primers) used in this Example are:

```
SA_F1
                                            (SEQ ID NO: 8)
5'-TGTTAGAATTTGAACAAGGATTTAAIIIIITAGCGACTTT-3'

SA_TSG(6)
                                            (SEQ ID NO: 5)
5'-[6-FAM]CATTCCG[T(BHQ-1)]GGTCAATCATTCGGTT-3'

SA_TSG(21)
                                            (SEQ ID NO: 6)
5'-[6-FAM]CATTCCGTGGTCAATCATTCGG[T(BHQ-1)]T-3'
```

(I represents deoxyinosine and the number 6 or 21 in the parenthesis means the distance of nucleotides between a reporter molecule and a quencher molecule)

The real-time PCR reaction was conducted as the protocol used for *S. pneumoniae* detection, except for template (*S.*

*aureus*), forward primer (SEQ ID NO: 8) and TSG primers (SEQ ID NO: 5 or 6) as reverse primers.

As shown in FIG. 8, fluorescent signals for *S. aureus* were observed in the presence of *S. aureus* template (Nos. 1 and 3) in the real-time PCR reaction using TSG primers and a template-dependent DNA polymerase having no 5' to 3' nuclease activity, whereas there was no fluorescent signal in the negative controls without the target template (Nos. 2 and 4)

The TSG primer (SEQ ID NO: 6) having a reporter molecule at 21 nucleotides apart from a quencher molecule showed lower Ct values and higher RFU values than the TSG primer (SEQ ID NO: 5) having a reporter molecule at 6 nucleotides apart from a quencher molecule.

C. Real-Time PCR for the Detection of *N. gonorrhoeae* Gene

When the target nucleic acid sequence of the *N. gonorrhoeae* is used as a template, the sequences of a forward primer and TSG primers (as reverse primers) used in this Example are:

```
NG_F1
                                          (SEQ ID NO: 9)
5'-TACGCCTGCTACTTTCACGCTIIIIIGTAATCAGAT-3'

NG_TSG(4)
                                         (SEQ ID NO: 10)
5'-[6-FAM]CTCAT[T(BHQ-1)]GGCGTGTTTCGCATATTTAAG-3'

NG_TSG(22)
                                         (SEQ ID NO: 11)
5'-[6-FAM]CTCATTGGCGTGTTTCGCATATT[T(BHQ-1)]AAG-3'
```

(I represents deoxyinosine and the number 4 or 22 in the parenthesis means the distance of nucleotides between a reporter molecule and a quencher molecule)

The real-time PCR reaction was conducted as the protocol used for *S. pneumoniae* detection, except for template (*N. gonorrhoeae*), a forward primer (SEQ ID NO: 9) and TSG primers (SEQ ID NO: 10 or 11) as reverse primers.

As shown in FIG. 9, fluorescent signals for *N. gonorrhoeae* were observed in the presence of *N. gonorrhoeae* template (Nos. 1 and 3) in the real-time PCR reaction using TSG primers and a template-dependent DNA polymerase having no 5' to 3' nuclease activity, whereas there was no fluorescent signal in the negative controls without the target template (Nos. 2 and 4)

In addition, the TSG primer (SEQ ID NO: 11) having a reporter molecule at 22 nucleotides apart from a quencher molecule showed lower Ct values and higher RFU values than the TSG primer (SEQ ID NO: 10) having a reporter molecule at 4 nucleotides apart from a quencher molecule, as shown in FIG. 9.

D. Real-Time PCR for the Detection of *N. meningitidis* Gene

When the target nucleic acid sequence of the *N. meningitidis* is used as a template, the sequences of a reverse primer and TSG primers (as forward primers) used in this Example are:

```
NM_R1
                                         (SEQ ID NO: 12)
5'-CCATAACCTTGAGCAATCCAIIIIICCTGACGTTC-3'

NM_TSG(7)
                                         (SEQ ID NO: 13)
5'-[6-FAM]CTTATCGC[T(BHQ-1)]TTCTGAAGCCATTG-3'

NM_TSG(20)
                                         (SEQ ID NO: 14)
5'-[6-FAM]CTTATCGCTTTCTGAAGCCAT[T(BHQ-1)]G-3'
```

(I represents deoxyinosine and the number 7 or 20 in the parenthesis means the distance of nucleotides between a reporter molecule and a quencher molecule)

The real-time PCR reaction was conducted as the protocol used for *S. pneumoniae* detection, except for template (*N. meningitidis*), a reverse primer (SEQ ID NO: 12) and TSG primers (SEQ ID NO: 13 or 14) as forward primers.

As shown in FIG. 10, fluorescent signals for *N. meningitidis* were observed in the presence of *N. meningitidis* template (Nos. 1 and 3) in the real-time PCR reaction using TSG primers and a template-dependent DNA polymerase having no 5' to 3' nuclease activity, whereas there was no fluorescent signal in the negative controls without the target template (Nos. 2 and 4)

In addition, the TSG primer (SEQ ID NO: 14) having a reporter molecule at 20 nucleotides apart from a quencher molecule showed lower Ct values and higher RFU values than the TSG primer (SEQ ID NO: 13) having a reporter molecule at 7 nucleotides apart from a quencher molecule, as shown in FIG. 10.

Example 3: The Real-Time PCR Sensitivity Using the TSG Primer and DNA Polymerase Having No 5' to 3' Exonuclease Activity for the Detection of *S. aureus*

The real-time PCR sensitivity using the TSG primer and DNA polymerase having no 5' to 3' exonuclease activity was tested by detecting the target nucleic acid sequences of *S. aureus* gene. For this study, the TSG primer (SEQ ID NO: 6) as a reverse primer was used in the real-time PCR reaction. The serially diluted (10-fold dilution) genomic DNA of *S. aureus* from 100 pg to 10 fg was used as a template.

The sequences of a forward primer and the TSG primer (as a reverse primer) used in this Example are:

```
SA_F1
                                          (SEQ ID NO: 8)
5'-TGTTAGAATTTGAACAAGGATTTAAIIIIITAGCGACTTT-3'

SA_TSG(21)
                                          (SEQ ID NO: 6)
5'-[6-FAM]CATTCCGTGGTCAATCATTCGG[T(BHQ-1)]T-3'
```

(I represents deoxyinosine and the number 21 in the parenthesis means the distance of nucleotides between a reporter molecule and a quencher molecule)

The real-time PCR reaction was conducted in the final volume of 20 μl containing diluted genomic DNA (from 100 pg to 10 fg; 10-fold dilution) of *S. aureus*, 2 μl of 10× Stoffel buffer containing 100 mM Tris-HCl (pH 8.3) and 100 mM KCl, 1 unit of AmpliTaq® DNA polymerase, Stoffel Fragment (Applied BioSystems, USA), 200 μM each of four dNTPs (dATP, dCTP, dGTP and dTTP), 5 mM of $MgCl_2$, 5 pmole of forward primer (SEQ ID NO: 8) and 5 pmole of TSG primer (SEQ ID NO: 6) as a reverse primer; the tube containing the reaction mixture was placed in the real-time thermocycler (CFX96, Bio-Rad); the reaction mixture was denatured for 2 min at 95° C. and subjected to 40 cycles of 30 s at 94° C., 60 s at 55° C. and 10 s at 72° C. Detection of the generated signal was performed at the annealing step (55° C.) of each cycle.

As shown in FIG. 11, when real-time PCR was performed using the serial dilution of *S. aureus* genomic DNA as described in the FIG. 11, it could detect target nucleic acid sequence up to 100 fg (Nos. 1-4).

Example 4: Signal Generation by the 5'-Cleavage Reaction on 5'-End Portion of the TSG Primer by the Template-Dependent Nucleic Acid Polymerase Having 5' to 3' Exonuclease Activity We have found that labeled primers hybridized with target nucleic acid sequences undergo a 5'-cleaveage reaction on their 5'-end portion by the 5' to 3' nuclease activity of a template-dependent nucleic acid polymerase and the 5'-cleaveage reaction intricately adopts to detection of target nucleic acid sequences by generating signals for target sequences (see PCT/KR2009/007064).

Therefore, we examined whether signals are generated by the 5'-cleaveage reaction on 5'-end portion of the TSG primer by the template-dependent nucleic acid polymerase having the 5' to 3' exonuclase activity.

To test this evaluation, we used *S. pneumoniae* as a target template and for experimental convenience, the synthetic oligonucleotide was used as a template for *S. pneumoniae* gene. Two TSG primers having different distances between a reporter molecule and a quencher molecule were examined respectively. 6-FAM (6-carboxyfluoresceine) was used as a fluorescent reporter molecule and located at 5'-end of TSG primers. Black Hole quencher 1 (BHQ-1) was used as a quencher molecule. Nucleic acid synthesis reaction was conducted with the repetition of denaturation, hybridization and primer extension. The signal was measured at the hybridization step of each repetition. Stoffel Fragment lacking intrinsic 5' to 3' exonuclease activity and Taq DNA polymerase having 5' to 3' exonuclease activity were used as the DNA polymerases.

The sequences of the synthetic template and the TSG primers used in this Example are:

```
SP_T105
                                         (SEQ ID NO: 1)
5'-TTACTGAAAGACAATGAAGACAACCTAACAGGGGAAGATGTTCGCG

AAGGCTTAACTGCAGTTATCTCAGTTAAACACCCAAATCCACAGTTTGA

AGGACAAACC-3'

SP_TSG(9)
                                         (SEQ ID NO: 2)
5'-[6-FAM]TCCTTCAAAC[T(BHQ-1)]GTGGATTTGGGTGT-3'

SP_TSG(21)
                                         (SEQ ID NO: 3)
5'-[6-FAM]TCCTTCAAACTGTGGATTTGGG[T(BHQ-1)]GT-3'
```

(The number 9 or 21 in the parenthesis means the distance of nucleotides between a reporter molecule and a quencher molecule)

A. Nucleic Acid Synthesis Reaction with the Repetition of Denaturation, Hybridization and Primer Extension Using DNA Polymerase Having No 5' to 3' Exonuclease Activity The nucleic acid synthesis reaction was conducted in the final volume of 20 μl containing 2 pmole of template (SEQ ID NO: 1), 2 μl of 10× Stoffel buffer [containing 100 mM Tris-HCl (pH 8.3) and 100 mM KCl], 1 unit of AmpliTaq® DNA polymerase, Stoffel Fragment (Applied BioSystems, USA), 200 μM each of four dNTPs (dATP, dCTP, dGTP and dTTP), 5 mM of MgCl$_2$ and 5 pmole of TSG primer (SEQ ID NO: 2 or 3); the tube containing the reaction mixture was placed in the real-time thermocycler (CFX96, Bio-Rad); the reaction mixture was denatured for 2 min at 95° C. and subjected to 40 cycles of 30 s at 94° C. and 60 s at 50° C. Detection of the generated signal was performed at the annealing step (50° C.) of each cycle.

In FIG. 12 showing the results after normalization, signal changes were not observed even in the presence of template (Nos. 1 and 5) where Stoffel Fragment lacking intrinsic 5' to 3' exonuclease activity was used as a DNA polymerase.

These results indicate that the signal intensity generated only by hybridization and primer extension was not changed over the reaction cycles because the template was not amplified during the nucleic acid reaction.

Therefore, it would be recognized that only hybridization and extension of a TSG primer in nucleic acid synthesis reactions with cycles is not able to accumulate detectable signals even in the presence of target nucleic acid sequences (Nos. 1 and 5).

B. Nucleic Acid Synthesis Reaction with the Repetition of Denaturation, Hybridization, and Primer Extension Using DNA Polymerase Having 5' to 3' Exonuclease Activity The nucleic acid synthesis reaction was conducted in the final volume of 20 μl containing 2 pmole of template (SEQ ID NO: 1), 10 μl of 2× DiastarTaq PCR Master Mix (Solgent, Korea) containing [MgCl$_2$ 12 mM, DiastarTaq PCR buffer, 2 U of DiastarTaq DNA polymerase and dNTP mix], 5 pmole of TSG primer (SEQ ID NO: 2 or 3); the tube containing the reaction mixture was placed in the real-time thermocycler (CFX96, Bio-Rad); the reaction mixture was denatured for 15 min at 95° C. and subjected to 40 cycles of 30 s at 94° C. and 60 s at 50° C. Detection of the generated signal was performed at the annealing step (50° C.) of each cycle.

As shown in FIG. 12, signal changes for *S. pneumoniae* were observed (Nos. 3 and 7) where Taq DNA polymerase having the 5' to 3' exonuclease activity were used as a DNA polymerase.

These results indicate that the utilization of the template-dependent polymerase having the 5' to 3' exonuclease activity is able to induce the 5'-cleavage reaction on 5'-end portion of the TSG primer. Accordingly, signals from the labeled fragments released from the TSG primers are generated and accumulated in every cycle, resulting in the observable signals indicating the presence of the target nucleic acid sequence (Nos. 3 and 7).

In the meantime, the TSG primer (SEQ ID NO: 2) having a reporter molecule at 9 nucleotides apart from a quencher molecule showed lower Ct values than the TSG primer (SEQ ID NO: 3) having a reporter molecule at 21 nucleotides apart from a quencher molecule. These results suggest that the TSG primers with shorter length between a reporter and a quencher exhibit larger changes in a quenching extent before and after the 5'-cleavage reaction than those with longer length between a reporter and a quencher.

Example 5: Examination of the TSG Primer with DNA Polymerase Having 5' to 3' Exonuclease Activity Under the Conditions of Real-Time PCR Reaction for the Detection of a Target Nucleic Acid We further examined whether the TSG primer can generate a signal sufficient to detect a target nucleic acid sequence during real-time PCR reaction using a template-dependent nucleic acid polymerase having 5' to 3' exonuclease activity.

To examine this evaluation, the same templates and primers used in Example 2 were used except for the template-dependent nucleic acid polymerase having 5' to 3' exonuclease activity and the reaction conditions.

A. Real-Time PCR for the Detection of *S. pneumoniae*

The real-time PCR was conducted in the final volume of 20 μl containing 10 ng of genomic DNA of *S. pneumoniae*, 10 μl of 2× DiastarTaq PCR Master Mix (Solgent, Korea) containing [MgCl$_2$ 12 mM, DiastarTaq PCR buffer, 2 U of DiastarTaq DNA polymerase and dNTP mix], 5 pmole of forward primer (SEQ ID NO: 7) and 5 pmole of TSG primer (SEQ ID NO: 2 or 3) as a reverse primer; the tube containing the reaction mixture was placed in the real-time thermocycler (CFX96, Bio-Rad); the reaction mixture was denatured for 15 min at 95° C. and subjected to 30 cycles of 30 s at 94° C., 60 s at 55° C. and 10 s at 72° C. Detection of the generated signal was performed at the annealing step (55° C.) of each cycle.

As shown in FIG. 13, fluorescent signals for *S. pneumoniae* were observed in the presence of *S. pneumoniae* template (Nos. 1 and 3), whereas there was no fluorescent signal in the negative controls without the template (Nos. 2 and 4).

In addition, the TSG primer (SEQ ID NO: 3) having a reporter molecule at 21 nucleotides apart from a quencher molecule showed lower Ct values and higher RFU values than the TSG primer (SEQ ID NO: 2) having a reporter molecule at 9 nucleotides apart from a quencher molecule.

B. Real-Time PCR for the Detection of *S. aureus*

The real-time PCR reaction was conducted as the protocol used for *S. pneumoniae* detection, except for template (*S. aureus*), forward primer (SEQ ID NO: 8) and TSG primers (SEQ ID NO: 5 or 6) as reverse primers.

As shown in FIG. 14, fluorescent signals for *S. aureus* were observed in the presence of *S. aureus* template (Nos. 1 and 3), whereas there was no fluorescent signal in the negative controls without the template (Nos. 2 and 4). In addition, the TSG primer (SEQ ID NO: 6) having a reporter molecule at 21 nucleotides apart from a quencher molecule showed lower Ct values and higher RFU values than the TSG primer (SEQ ID NO: 5) having a reporter molecule at 6 nucleotides apart from a quencher molecule.

C. Real-Time PCR for the Detection of *N. gonorrhoeae*

The real-time PCR reaction was conducted as the protocol used for *S. pneumoniae* detection, except for template (*N. gonorrhoeae*), forward primer (SEQ ID NO: 9) and TSG primers (SEQ ID NO: 10 or 11) as reverse primers.

As shown in FIG. 15, fluorescent signals for *N. gonorrhoeae* were observed in the presence of *N. gonorrhoeae* template (Nos. 1 and 3), whereas there was no fluorescent signal in the negative controls without the template (Nos. 2 and 4). In addition, the TSG primer (SEQ ID NO: 11) having a reporter molecule at 22 nucleotides apart from a quencher molecule showed lower Ct values and higher RFU values than the TSG primer (SEQ ID NO: 10) having a reporter molecule at 4 nucleotides apart from a quencher molecule.

D. Real-Time PCR for the Detection of *N. meningitidis*

The real-time PCR reaction was conducted as the protocol used for *S. pneumoniae* detection, except for template (*N. meningitidis*), reverse primer (SEQ ID NO: 12) and TSG primers (SEQ ID NO: 13 or 14) as forward primers.

As shown in FIG. 16, fluorescent signals for *N. meningitidis* were observed in the presence of *N. meningitidis* template (Nos. 1 and 3), whereas there was no fluorescent signal in the negative controls without the template (Nos. 2 and 4). In addition, the TSG primer (SEQ ID NO: 14) having a reporter molecule at 20 nucleotides apart from a quencher molecule showed lower Ct values and higher RFU values than the TSG primer (SEQ ID NO: 13) having a reporter molecule at 7 nucleotides apart from a quencher molecule.

In conclusion, where a template-dependent DNA polymerase having 5' to 3' nuclease activity is used, signals indicative of the presence of the target nucleic acid sequence can be present in two other fashions: (i) signal generation by signal unquenching of the interactive label system on the TSG primer caused by conformation change upon hybridization with the target nucleic acid sequence; and (ii) signal generation by the 5'-cleaveage reaction on its 5'-end portion of the TSG primer by the template-dependent nucleic acid polymerase having the 5' to 3' nuclease activity.

Example 6: The Real-Time PCR Sensitivity Using the TSG Primer and DNA Polymerase Having 5' to 3' Exonuclease Activity for the Detection of *S. aureus*

The real-time PCR sensitivity using the TSG primer and DNA polymerase having 5' to 3' exonuclease activity was tested by detecting the target nucleic acid sequences of *S. aureus* gene. To examine this evaluation, the same templates and primers used in Example 3 were used except for the template-dependent nucleic acid polymerase having 5' to 3' exonuclease activity and the reaction conditions.

The real-time PCR was conducted in the final volume of 20 μl containing diluted genomic DNA (from 100 pg to 10 fg; 10-fold dilution) of genomic DNA of *S. aureus*, 10 μl of 2× QuantiTect Multiplex PCR Master Mix (Qiagen) containing [MgCl$_2$ 11 mM, QuantiTect Multiplex PCR buffer, HotstartTaq DNA polymerase and dNTP mix], 5 pmole of forward primer (SEQ ID NO: 8) and 5 pmole of TSG primer (SEQ ID NO: 6) as a reverse primer; the tube containing the reaction mixture was placed in the real-time thermocycler (CFX96, Bio-Rad); the reaction mixture was denatured for 15 min at 95° C. and subjected to 40 cycles of 30 s at 94° C., 60 s at 55° C. and 10 s at 72° C. Detection of the generated signal was performed at the annealing step (55° C.) of each cycle.

As shown in FIG. 17, when real-time PCR was performed using the serial dilution of *S. aureus* genomic DNA as described in the FIG. 11, it could detect target nucleic acid sequence up to 100 fg (Nos. 1-4).

Example 7: Evaluation of the TSG Primer for the Detection of Target Nucleic Acid Sequence on Chip When the target nucleic acid sequence of the *S. pneumoniae* gene is used as a template, the sequences of the synthetic template and the TSG primers used in this Example are:

SP_T105

(SEQ ID NO: 1)

5'-TTACTGAAAGACAATGAAGACAACCTAACAGGGGAAGATGTTCGCG

AAGGCTTAACTGCAGTTATCTCAGTTAAACACCCAAATCCACAGTTTGA

AGGACAAACC-3'

SP_TSG(21)_S (SEQ ID NO: 15)

5'-[AminoC6]TTTTT[T(Fluoresceine)]CCTTCAAACTGTGGA

TTTGGG[T(BHQ-1)]GT (The number 21 in the parenthesis means the distance of nucleotides between a reporter molecule and a quencher molecule)

A. Immobilization of the TSG Primer on Chip Slide

The TSG primer (SEQ ID NO: 15) was dissolved to a final concentration of 50 uM in Genorama Spotting Solution Type I. The dissolved TSG primer was spotted onto a glass slide (Genorama, Estonia) at room temperature and 70% relative humidity. The slide was incubated in a humid chamber at 37° C. for 2 hours. Then, the slide was soaked in 1% ammonium solution for 10 minutes, followed by washing with distilled water at room temperature.

B. Nucleic Acid Synthesis Reaction on Chip

The nucleic acid synthesis reaction was conducted in the final volume of 20 μl containing 2 pmole of template (SEQ ID NO: 1), 2 μl of 10× Stoffel buffer [containing 100 mM Tris-HCl (pH 8.3) and 100 mM KCl], 1 unit of AmpliTaq® DNA polymerase, Stoffel Fragment (Applied BioSystems, USA), 200 μM each of four dNTPs (dATP, dCTP, dGTP and dTTP), 5 mM of MgCl$_2$; the reaction mixture was transferred to the slide. The slide was placed in in situ PCR machine (GeneAmp in situ, Perkin Elmer); the slide was incubated for 2 min at 95° C. for denaturation and subjected to 40 min at 50° C. Following the nucleic acid synthesis reaction, the slide was washed (at 70° C.) and the signals of the slide were detected through a microarray scanner (ScanArray4000, Perkin Elmer), followed by analysis of the images.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA or a mixture of nucleic acids using a target signal generating primer (TSG primer) in an amplification reaction:

wherein said target signal generating primer (TSG primer) is not immobilized on a solid substrate; and wherein said amplification reaction is in a liquid phase;

said method comprising the steps:

(a) hybridizing the target nucleic acid sequence with a primer pair composed of two primers as a forward primer and a reverse primer capable of amplifying the target nucleic acid sequence; wherein at least one of the two primers is the TSG primer; wherein the TSG primer comprises (i) a hybridizing nucleotide sequence complementary to the target nucleic acid sequence and (ii) a dual label system consisting of a single reporter molecule and a single non-fluorescent quencher molecule; wherein either or both of the reporter molecule and the quencher molecule is/are located on the hybridizing nucleotide sequence; wherein the reporter molecule and the quencher molecule are positioned at 6-40 nucleotides apart from each other; wherein the TSG primer is a single stranded oligonucleotide and has no substantial self-complementary sequence such that the TSG primer does not comprise hairpin loop structure(s) when it is not hybridized with the target nucleic acid sequence; wherein when the TSG primer is not hybridized with the target nucleic acid sequence, the reporter molecule and the quencher molecule are three-dimensionally adjacent to each other in a twist conformation, without assist by hairpin loop structure(s), to allow the quencher molecule to quench a signal from the reporter molecule, thereby generating no signal indicative of the presence of the target nucleic acid sequence; wherein when the TSG primer is hybridized with the target nucleic acid sequence, the reporter molecule and the quencher molecule are three-dimensionally separated in a stretch conformation to allow the quencher molecule to unquench the signal from the reporter molecule, whereby the signal indicative of the presence of the target nucleic acid sequence is generated and obtained without cleavage of the TSG primer before extension of the primer pair wherein the TSG primer does not comprise a minor groove binder (MGB);

(b) contacting the resultant of step (a) to a template-dependent nucleic acid polymerase under primer extension conditions such that the 3'-extension reaction at the 3'-ends of the two primers is induced;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal indicates the presence of the target nucleic acid sequence; wherein at least some of the amplified target nucleic acid products comprises the reporter molecule and the quencher molecule remaining attached to the TSG primer, and the reporter molecule and the quencher molecule on the amplified target nucleic acid products provide the signal indicative of the presence of the target nucleic acid sequence; and wherein the method does not further include any other oligonucleotide comprising a hybridizing nucleotide sequence complementary to the target nucleic acid sequence.

2. The method according to claim 1, wherein the template-dependent nucleic acid polymerase is a template-dependent nucleic acid polymerase having no 5' to 3' nuclease activity.

3. The method according to claim 1, wherein the reporter molecule or the quencher molecule on the TSG primer is located at its 5'-end or at 1-5 nucleotides apart from its 5'-end.

4. The method according to claim 1, wherein the template-dependent nucleic acid polymerase is a template-dependent nucleic acid polymerase having a 3' to 5' exonuclease activity.

5. The method according to claim 4, wherein the TSG primer has at least one mismatch nucleotide having a backbone resistant to the 3' to 5' nuclease activity of template-dependent nucleic acid polymerases at its 3'-end portion.

6. A method for detecting at least two types of target nucleic acid sequences from a DNA or a mixture of nucleic acids using a target signal generating primer (TSG primer) not immobilized on a solid substrate in an amplification reaction in a liquid phase, comprising the steps of:

(a) hybridizing the at least two types of target nucleic acid sequences with at least two primer pairs, each primer pair being composed of two primers as a forward primer and a reverse primer capable of amplifying each of the target nucleic acid sequences; wherein at least one of the two primers is the TSG primer; wherein the TSG primer comprises (i) a hybridizing nucleotide sequence complementary to the target nucleic acid sequence and (ii) a dual label system consisting of a single reporter molecule and a single non-fluorescent quencher molecule; wherein either or both of the reporter molecule and the quencher molecule is located on the hybridizing nucleotide sequence; wherein the reporter molecule and the quencher molecule are positioned at 6-40 nucleotides apart from each other; wherein the TSG primer is a single-stranded oligonucleotide, and has no substantial self-complementary sequence such that the TSG primer does not comprise hairpin loop structure(s) when it is not hybridized with the target nucleic acid sequence; wherein when the TSG primer is not hybridized with the target nucleic acid sequence, the reporter molecule and the quencher molecule are three-dimensionally adjacent to each other in a twist conformation with no help of hairpin loop structures to allow the quencher molecule to quench a signal from the reporter molecule, thereby generating no signal indicative of the presence of the target nucleic acid sequence; wherein when the TSG primer is hybridized with the target nucleic acid sequence, the reporter molecule and the quencher molecule are three-dimensionally separated in a stretch conformation to allow the quencher molecule to unquench the signal from the reporter molecule, whereby the signal indicative of the presence of the target nucleic acid sequence is generated and obtained without cleavage of the TSG primer before extension of the primer pair; wherein the TSG primer does not comprise a minor groove binder (MGB);

(b) contacting the resultant of step (a) to a template-dependent nucleic acid polymerase under primer extension conditions such that the 3'-extension reaction at the 3'-ends of the two primers is induced;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal indicates the presence of the target nucleic acid sequence; wherein at least some of the amplified target nucleic acid products comprises the reporter molecule and the quencher molecule remaining attached to the TSG primer, and the reporter molecule and the quencher molecule on the amplified target nucleic acid products provide the signal indicative of the presence of the target nucleic acid sequence; wherein the method does not further include any other oligonucleotide comprising a hybridizing nucleotide sequence complementary to the at least two types of target nucleic acid sequences.

7. The method according to claim 1, wherein the target nucleic acid sequence comprises a nucleotide variation.

* * * * *